(12) United States Patent
Hsu et al.

(10) Patent No.: US 9,808,556 B2
(45) Date of Patent: *Nov. 7, 2017

(54) BIOCOMPATIBLE AND BIODEGRADABLE ELASTOMER

(71) Applicant: National Taiwan University, Taipei (TW)

(72) Inventors: Shan-hui Hsu, Taipei (TW); Kun-Che Hung, Taipei (TW)

(73) Assignee: National Taiwan University, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/195,578

(22) Filed: Jun. 28, 2016

(65) Prior Publication Data

US 2016/0303279 A1 Oct. 20, 2016

Related U.S. Application Data

(63) Continuation-in-part of application No. 14/145,393, filed on Dec. 31, 2013.

(30) Foreign Application Priority Data

Jan. 2, 2013 (TW) .............................. 102100076 A

(51) Int. Cl.
| | |
|---|---|
| *A61L 27/18* | (2006.01) |
| *A61L 27/52* | (2006.01) |
| *A61F 2/06* | (2013.01) |
| *A61L 27/58* | (2006.01) |
| *C08G 18/40* | (2006.01) |
| *C08G 18/42* | (2006.01) |
| *C08G 18/75* | (2006.01) |
| *A61L 27/56* | (2006.01) |

(52) U.S. Cl.
CPC .............. *A61L 27/18* (2013.01); *A61L 27/52* (2013.01); *A61L 27/56* (2013.01); *A61L 27/58* (2013.01); *C08G 18/4018* (2013.01); *C08G 18/4202* (2013.01); *C08G 18/755* (2013.01); *A61F 2210/0004* (2013.01); *C08G 2230/00* (2013.01)

(58) Field of Classification Search
CPC .. C08L 75/04; C08L 18/4277; C08L 18/4833; C08L 18/664; C08L 2230/00; A61L 26/0019; A61L 27/18; A61L 31/06
See application file for complete search history.

(56) References Cited

U.S. PATENT DOCUMENTS

| | | | | |
|---|---|---|---|---|
| 4,098,743 | A * | 7/1978 | Scriven .............. | C08G 18/0819 524/590 |
| 6,177,523 | B1 * | 1/2001 | Reich .................... | C08G 18/10 525/450 |
| 2008/0262613 | A1 * | 10/2008 | Gogolewski ........ | A61L 26/0019 623/11.11 |
| 2009/0175921 | A1 * | 7/2009 | Gunatillake ............ | A61L 27/18 424/423 |
| 2009/0263457 | A1 * | 10/2009 | Trollsas .................. | A61L 31/10 424/426 |

OTHER PUBLICATIONS

Yi-Chun Tsai et al., Synthesis of Thermoresponsive Amphiphilic Polyurethane Gel as a New Cell Printing Material near Body Temperature, ACS Appl. Mater. Interfaces 2015, 7, 27613-27623.

* cited by examiner

*Primary Examiner* — Anna Falkowitz
(74) *Attorney, Agent, or Firm* — WPAT, P.C., Intellectual Property Attorneys; Anthony King

(57) ABSTRACT

The present invention provides a biocompatible and biodegradable elastomer, comprising a hard segment and a soft segment. The hard segment is formed by reacting diisocyanate and a chain extender; and the soft segment is comprising a biodegradable oligomer diol, wherein the biodegradable oligomer diol is selected from the group consisting of polycaprolactone diol, polyethylene butylene adipate diol (PEBA diol), poly-L-lactic acid diol (PLLA diol), polylactic acid diol and any combination thereof. The biocompatible and biodegradable elastomer of present invention can be used to produce vascular graft, cell carrier, drug carrier or gene carrier.

14 Claims, 28 Drawing Sheets

SEQUENCE LISTING

<160> NUMBER OF SEQ ID NOS: 12

<210> SEQ ID NO 1
<211> LENGTH: 24
<212> TYPE: DNA
<213> ORGANISM: Artificial sequence
<220> FEATURE:
<223> OTHER INFORMATION: murine IL-1 primer (forward)

<400> SEQUENCE: 1
cccaagcaat acccaaagaa gaag                    24

<210> SEQ ID NO 2
<211> LENGTH: 22
<212> TYPE: DNA
<213> ORGANISM: Artificial sequence
<220> FEATURE:

<223> OTHER INFORMATION: murine IL-1 primer (reverse)

<400> SEQUENCE: 2
tgtcctgacc actgttgttt cc                                              22

<210> SEQ ID NO 3
<211> LENGTH: 21
<212> TYPE: DNA
<213> ORGANISM: Artificial sequence
<220> FEATURE:
<223> OTHER INFORMATION: murine IL-6 primer (forward)

<400> SEQUENCE: 3
ttccatccag ttgccttctt g                                               21

<210> SEQ ID NO 4
<211> LENGTH: 22
<212> TYPE: DNA
<213> ORGANISM: Artificial sequence
<220> FEATURE:
<223> OTHER INFORMATION: murine IL-6 primer (reverse)

<400> SEQUENCE: 4
tcatttccac gatttcccag ag                                              22

<210> SEQ ID NO 5
<211> LENGTH: 20
<212> TYPE: DNA
<213> ORGANISM: Artificial sequence
<220> FEATURE:
<223> OTHER INFORMATION: murine TNF- \ primer (forward)

<400> SEQUENCE: 5
cgagtgacaa gcctgtagcc                                                 20

<210> SEQ ID NO 6
<211> LENGTH: 23
<212> TYPE: DNA
<213> ORGANISM: Artificial sequence
<220> FEATURE:
<223> OTHER INFORMATION: murine TNF- \-32-primer (reverse)

<400> SEQUENCE: 6
ttgaagagaa cctgggagta gac                                             23

<210> SEQ ID NO 7
<211> LENGTH: 21
<212> TYPE: DNA
<213> ORGANISM: Artificial sequence
<220> FEATURE:
<223> OTHER INFORMATION: murine ]-actin primer (forward)

<400> SEQUENCE: 7
tcctgtggca tccacgaaac t                                               21

<210> SEQ ID NO 8
<211> LENGTH: 21
<212> TYPE: DNA
<213> ORGANISM: Artificial sequence
<220> FEATURE:
<223> OTHER INFORMATION: murine ]-actin primer (reverse)

<400> SEQUENCE: 8
ggagcaatga tcctgatctt c                                               21

```
<210> SEQ ID NO 9
<211> LENGTH: 31
<212> TYPE: DNA
<213> ORGANISM: Artificial sequence
<220> FEATURE:
<223> OTHER INFORMATION: bovine eNOS primer (forward)

<400> SEQUENCE: 9
tagaattccc agcacctttg ggaatggcga t                              31

<210> SEQ ID NO 10
<211> LENGTH: 37
<212> TYPE: DNA
<213> ORGANISM: Artificial sequence
<220> FEATURE:
<223> OTHER INFORMATION: bovine eNOS primer (reverse)

<400> SEQUENCE: 10
atagaattgg attcacttct gtgttgctgg actcctt                        37

<210> SEQ ID NO 11
<211> LENGTH: 20
<212> TYPE: DNA
<213> ORGANISM: Artificial sequence
<220> FEATURE:
<223> OTHER INFORMATION: bovine  ]-actin primer (forward)

<400> SEQUENCE: 11
aaagacagct atgtgggaga                                           20

<210> SEQ ID NO 12
<211> LENGTH: 19
<212> TYPE: DNA
<213> ORGANISM: Artificial sequence
<220> FEATURE:
<223> OTHER INFORMATION: bovine  ]-actin primer (reverse)

<400> SEQUENCE: 12
atgatctggg tcatcttct                                            19
```

BIOCOMPATIBLE AND BIODEGRADABLE ELASTOMER

CROSS-REFERENCES TO RELATED APPLICATIONS

This application is a continuation-in-part of U.S. patent application Ser. No. 14/145,393, filed on Dec. 31, 2013, which claims the priority benefit of Taiwan Patent Application No. 102100076 filed on 2 Jan. 2013. The entirety of each of the above-mentioned patent applications is hereby incorporated by reference herein and made a part of this specification.

BACKGROUND OF THE INVENTION

1. Field of the Invention

The present invention relates to a biocompatible and biodegradable elastomer, and, particularly, a biocompatible and biodegradable elastomer suitable for the use of vascular graft.

2. The Prior Arts

Vascular graft can serve as vascular transplant material and substitute specific blood vessel in human body that is damaged by aging or pathologies such as atherosclerosis; or serve as graft fistula for patients undergoing hemodialysis. Vascular transplant materials often used in general surgical operations can be biological vascular graft or synthetic vascular graft.

Biological vascular graft includes autologous transplantation grafts and allogenic transplantation grafts, in which autologous transplantation grafts are often originated from saphenous veins or internal mammary arteries. Although saphenous veins and internal mammary arteries are ideal material, the source is limited. Allogenic transplantation grafts, on the other hand are usually the chemically treated blood vessels taken from animal bodies. Although the source of allogenic transplantation graft is much abundant, thrombus, vascular tangles, and aneurysm are likely to occur upon transplanting into human bodies.

The development of synthesized vascular graft dated from the success of vinyl chloride-acrylonitrile copolymer fiber (Vinyon N) vascular graft introduced by Voorhees in 1952. It was also been proofed to be clinically applicable. Synthesized vascular graft can also be categorized into non-biodegradable or biodegradable vascular graft according to its material. With respect to biological vascular graft, synthesized vascular graft is unlikely to cause problems such as immune response, thrombus, or vascular calcification, thus is considered to be the more ideal vascular graft for transplantation.

Biomedical materials for the applications of vascular graft preparation should take into account of factors such as good biocompatibility, outstanding flexibility and compliance, appropriate pore size, and having functional endothelial layer. Vascular graft, according to the diameter, can be divided into large diameter (>8 mm) vascular graft, medium diameter (6 to 8 mm) vascular graft, and small diameter (<6 mm) vascular graft (or namely small vascular graft). Small vascular grafts with diameter less than 6 mm can be used to substitute blood vessels with lower blood flow such as arteriole, coronary artery, or groin artery, however, currently the replacement of arteriole or vein with small vascular graft yet to reach satisfactory results due to undesirable long-term patency, as well as problems such as inner layer thickening of angiogensis and vascular narrowing or blocking. Hence, the development of small vascular grafts that possess similar characteristics to human artery and vein as well as good biocompatibility to minimize problems of inner layer thickening of the newborn vessel is a critical task for modern vascular graft engineering.

Biodegradable elastomer is the macromolecule that exhibits advantages such as elasticity and biodegradability as well as good biocompatibility, mechanical property, and workability, and can be widely used in the field of biomedicine, for example, hard tissue embedding, repairing material, surgical suture, carrier for drug release, and vascular tissue engineering. Thus, the development of a biocompatible and biodegradable elastomer with features that can be used as vascular graft can dramatically promote the advance of vascular tissue engineering.

SUMMARY OF THE INVENTION

The accomplish the abovementioned industrial needs, the present invention provides a biocompatible and biodegradable elastomer, comprising: a main chain of polyurethane comprising a hard segment and a soft segment, the hard segment is formed by reaction of diisocyanate and a chain extender, and the soft segment is a biodegradable oligomer diol, wherein the biodegradable oligomer diol is selected from the group consisting of polycaprolactone diol, polyethylene butylene adipate diol, polylactic acid diol, and any combinations thereof.

In one embodiment of the present invention, the amount of the soft segment is between 45% and 75% w/w of the total weight of the elastomer. The polylactic acid diol is L-lactic acid or DL-lactic acid. When the soft segment is consisted of polycaprolactone diol and polyethylene butylene adipate diol, the polycaprolactone diol is in an amount of greater than 0.3 molar fraction of the degradable oligomer diol; when the soft segment is consisted of polycaprolactone diol and polylactic acid diol, the polycaprolactone diol is in an amount of greater than 0.4 molar fraction of the degradable oligomer diol; and when the soft segment is consisted of polycaprolactone diol and polylactic acid diol, the polycaprolactone diol is in an amount of greater than 0.8 molar fraction of the degradable oligomer diol. The diisocyanate is alicyclic polyisocyanate, and preferably, isophorone diisocyanate, whereas the chain extender is preferably ethylenediamine.

Another aspect of the present invention is to provide biocompatible and biodegradable elastic membrane made of the above biocompatible and biodegradable elastomer, wherein the Young's modulus of the biocompatible and biodegradable elastic membrane is greater than 0.5 MPa and smaller than 40 MPa, the tensile strength of the biocompatible and biodegradable elastic membrane is greater than 5 MPa and less than 50 MPa, the elongation of the biodegradable elastic membrane is greater than 400%.

Another aspect of the present invention is to provide a vascular graft made of the above biocompatible and biodegradable elastomer, wherein a plurality of pores are present on the wall of the vascular graft with an average pore diameter on the outer surface is between 5 to 50 µm, and an average pore diameter on the cross-section is between 10 to 100 µm. The elongation of the vascular graft is greater than 220%, and the pores are made by using freeze drying or particle-leaching method; additionally, the surface of the wall of the vascular graft can be chemically modified.

Another aspect of the present invention is to provide a carrier made of the above biocompatible and biodegradable elastomer, wherein the carrier is present in the form of microsphoere, hydrogel, nanodispersion, nanodispersion-coated inorganic nanoparticle, foam, electrospinning fiber, or scaffold. The carrier exhibits electronegativity, amphiphilicity, and anticoagulant ability and is used for carrying a cell, a gene, or a drug.

According to the technical features of the present invention, a biocompatible and biodegradable elastomer can be obtained, and the elastomer can further be made into scaffold which the diameters of the pores on the surface and the cross-section are within the range of the diameter of vascular graft endothelialization. Additionally, the scaffold not posses significant blood coagulation function. Endothelial cells and adipose-derived stem cells can be successfully implanted onto the scaffold and proliferate. The scaffold also exhibits good biocompatibility with no inflammatory response and low allogenic response, which indicates being an ideal material for vascular graft. Moreover, the characteristics of electronegativity and non-blood-platelet-activation of the biocompatible and biodegradable elastomer of the present invention indicating its anticoagulant ability.

On the other hand, the biocompatible and biodegradable elastomer of the present invention possesses good dispersion stability and blood compatibility. The biocompatible and biodegradable elastomer of the present invention from hydrogel by increasing temperature, or prepared in the form of microsphere, fiber, 3D foam, and sophisticated scaffold. This advantages of various waterborne workability allow the biocompatible and biodegradable elastomer of the present invention to be widely used in the field of biomedicine.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

BRIEF DESCRIPTION OF THE DRAWINGS

(FIG. 28A: 25° C.; FIG. 28B: 37° C.; and FIG. 28C: 50° C.).

DETAILED DESCRIPTION OF THE PREFERRED EMBODIMENT

Definition

Figure 1:
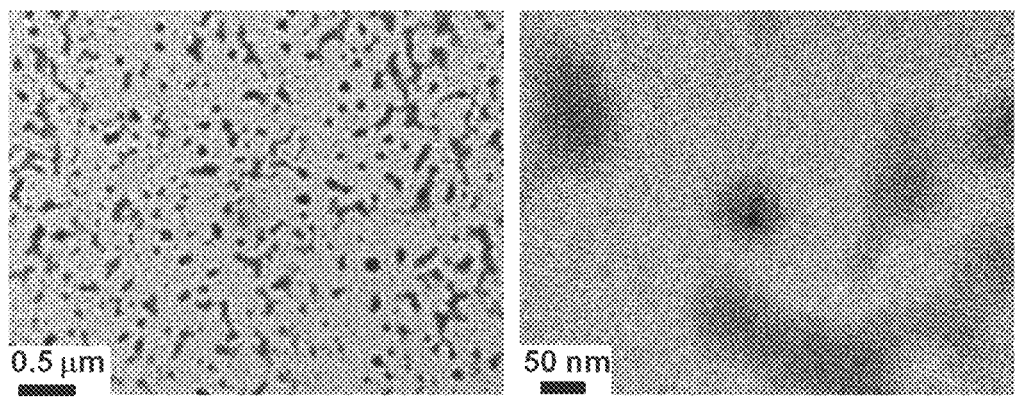
FIG. 1 is the TEM image of the waterborne biodegradable polyurethane emulsion.

As used herein, unless otherwise specified, the term "biocompatible and biodegradable polyurethane", "waterborne biodegradable polyurethane", "biodegradable polyurethane" or "biodegradable elastomer" refers to the "biocompatible and biodegradable elastomer" of the present invention.

As used herein, unless otherwise specified, the term "elastomer" refers to in the form of polyurethane nanoparticle (NP) dispersion, polyurethane emulsion or sol-gel.

As used herein, unless otherwise specified, the term "amphiphilicity" refers to the characteristic of being hydrophilic and hydrophobic simultaneously.

As used herein, the data provided represent experimental values that can vary within a range of ±20%, preferably within ±10%, and most preferably within ±5%.

One embodiment of the present invention is to prepare a biocompatible and biodegradable elastomer which is waterborne without cross-linking system, comprising a main chain of polyurethane which comprises a hard segment and a soft segment, the hard segment is formed by reaction of dissocyanate and a chain extender, and the soft segment is formed by reaction of a biodegradable oligomer diol and polycaprolactone diol (PCL diol). The biodegradable oligomer diol is polyethylene butylene adipate diol (PEBA diol) or polylactic acid diol. More specifically, the polylactic acid diol is poly-L-lactic acid diol (PLLA diol) or poly-DL-lactic acid diol (PDLLA diol).

The amount of the soft segment is between 45% and 75% w/w of the total weight of the biocompatible and biodegradable elstomer of the present invention, and in one embodiment of the present invention, the amount of the soft segment is represented by 65% w/w of the total weight of the biocompatible and biodegradable elastomer.

In another embodiment of the present invention, coating or grafting sulfonated chitosan onto the surface of the biocompatible and biodegradable elstomer is disclosed, and this material is made into tubular shape such as but not limited to artificial vascular graft, the elstomer can also be made into porous body, membrane, and cell scaffold.

The biocompatible and biodegradable elastomer of the present invention is used in the murine macrophage inflammatory test to proof that the biocompatible and biodegradable elastomer of the present invention does not activate macrophage and not cause inflammatory response. On the other hand, by the degradation test at 50° C. using PBS, the biocompatible and biodegradable elastomer of the present invention is proofed to exhibit higher degradation rate comparing to the polyurethane of the control groups. The biocompatible and biodegradable elastomer having different soft segments exhibit different degradation rate according to the components and proportions.

In another embodiment of the present invention, the biocompatible and biodegradable elastomer is made into scaffold by using electrospinning, freeze drying, and particle-leaching method. The diameter of pores on the surface and cross-section pores of the scaffold made using these three methods are within the pore diameter range required for vascular graft endothelialization, thus, the scaffolds made of the biocompatible and biodegradable elastomer are ideal material for vascular graft.

The abovementioned scaffold is subjected to biocompatibility test, in the endothelial cell adhesion and proliferation test, the scaffold made of the biocompatible and biodegradable elastomer of the present invention exhibits significant higher adhesion rate and proliferation rate comparing to the control group (TCPS medium), thus, can promote the adhesion and proliferation of endothelial cells, hence, promote the angiogensis. On the other hand, in the adipose-derived stem cell seeding rate test, the scaffold made of the biocompatible and biodegradable of the present invention shows significant higher seeding rate than the control group (PLA), indicating that cells can be successfully implanted onto the scaffold and can survive and proliferate without wet condition. In the blood platelet adhesion test, a tendency to decrease regarding blood platelet adhesion and activation can be observed after the surface modification, indicating that surface modification can suppress blood platelet adhesion and activation.

In the embodiments of the present invention, the terminology of the waterborne biodegradable polyurethane in different ratio is shown in Table 1. In addition, the waterborne biodegradable polyurethane made using electrospinning, freeze drying, or particle-leaching method incorporated with freeze drying are represented by using an upper index of e, f, or s, respectively, as suffixes; different waterborne biodegradable polyurethane with surface modification of sulfonated chitosan are represented by using "-ASC" as suffixes.

In embodiments of the present invention, experimental results are expressed as mean±standard error of the mean. Mean was analyzed using the t-test. Statistically significant difference was set at the level of $P<0.05$.

Example 1

Preparation of Degradable Elstomer

1-1 Formulation

The different soft segments were prepared by mixing three different degradable (water degradable) oligomer diols and polycaprolactone diol with several ratios so as to synthesize various degradable polyurethane in which the rate of degradation is controllable. The three different soft segments are shown in Table 1, where EB represents PEBA, LL represents PLLA and DL represents PDLLA. The soft segment with 20 wt % polylactic acid diol is shown in Table 2. Firstly, 4.4 wt % of 2,2-bis(hydroxymethyl)propionic acid (DMPA, Aldrich) was fixed. The molar ratio of isocyanate functional group and hydroxyl group of the prepolymer before water-dispersion was set at 1.9 (NCO/OH), while the molar ratio of isocyanate functional group and hydroxyl group plus amine group of the prepolymer after water-dispersion was set at 1.08 (NCO/(OH+$NH_2$)). Additionally, 85 mol % of chain extender with solid content of 30 wt % was added. The ratio of IPDI:marcodiols:DMPA:EDA:TEA was 3.76:1:1:1.51:1. The detailed formulation is shown in Table 3.

The waterborne biodegradable polyurethane PCL100 is formulated by replacing the proportion of soft segment or diol shown in Table 2 and Table 3 with 100% polycaprolactone diol. The PCL40EB60 is formulated by replacing the proportion of soft segment or diol shown in Table 2 and Table 3 with 40% polycaprolactone diol and 60% polyethylene butylene adipate diol.

TABLE 1

Different waterborne biodegradable polyurethane with Soft segments

| | Molar ratio of the soft segment | | | | |
|---|---|---|---|---|---|
| Sample | PCL diol | PEBA diol | PDLA diol | PLLA diol | Prepolymerization temperature (° C.) |
| PCL100 | 100 | — | — | — | 75 |
| PCL40EB60 | 40 | 60 | — | — | 75 |
| PCL80LL20 | — | 80 | — | 20 | 95 |
| PCL80DL20 | — | 80 | 20 | — | 75 |

TABLE 2

Waterborne biodegradable polyurethane with soft segment of 20 wt % polylactic acid

| Samples of waterborne biodegradable polyurethane | P-20 |
|---|---|
| Total weight (g) | 358 |
| Total solid weight (g) | 107 |
| Iso index before water-dispersion (NCO/OH) | 1.90 |
| Iso index after water-dispersion ((NCO/(OH + $NH_2$)) | 1.08 |
| amine mol % of prepolymerized NCO mol % | 85 |
| Solid content weight % | 30 |
| Solvent content weight % | 70 |
| Weight of hard segment % | 35 |
| Weight of PLA diol of the soft segment % | 13 |
| Weight of PCL diol of the soft segment % | 52 |

TABLE 3

Waterborne biodegradable polyurethane with soft segment of 20 wt % polylactic acid diol

| | Molecular weight (g/mol) | Molar ratio | Weight (g) |
|---|---|---|---|
| IPDI | 222.28 | 3.76 | 14.64 |
| DMPA | 134.13 | 1.00 | 2.345 |
| PCL diol | 2000 | 0.80 | 28.00 |
| PLA diol | 2000 | 0.20 | 7.00 |
| EDA | 60.1 | 1.51 | 1.60 |
| TEA | 101.19 | 1 | 1.77 |
| MEK | 72.11 | | 13.00 |
| $H_2O$ | 18.02 | | 110.26 |
| T-9 | 405.12 | | 0.05 |

1-2 Synthetic Process

The synthetic process was done by reacting polycaprolactone diol (PCL diol, Mw=2000 g/mol, Aldrich) with polyethylene butylene adipate diol (PEBA diol, Mw=2000 g/mol, GRECO), poly-L-lactic acid diol (PLLA diol, Mw=2000 g/mol) and poly-DL-lactic acid diol (PDLLA diol, Mw=2000 g/mol), respectively. The poly-L-lactic acid diol is obtained by the ring-opening reaction of L-lactide and 1,4-BDO in the molar ratio of 13:1 with the addition of catalyst, T-9, under 150° C. for 10 to 12 hours followed by temperature reduction to 0 to 4° C., ethanol purification, vacuum drying, and grinding. The poly-DL-lactic acid diol is obtained by the ring-opening reaction of DL-lactide and 1,4-BDO in the molar ratio of 13:1 with the addition of catalyst, T-9, under 150° C. for 10 to 12 hours followed by temperature reduction to 0 to 4° C. and vacuum sublimation in a controlled temperature of 120° C.

The above synthesized compounds were added to four-necked separable flask, adjusted to appropriate prepolymerization temperature, and mechanically homogenized at 180 rpm. After the reactant becoming a homogenized liquid, tin(II)2-ethylhexanoate (T-9, Alfa Aesar) and isophorone diisocyanate (IPDI, Evonik Degussa GmbH) were added as catalysts. The reactant was then stirred at 180 rpm. The reaction was proceeded at the prepolymerization temperature for 3 hours.

Then, the temperature is reduced to 75° C. and 2,2-bis (hydroxymethyl)propionic acid (DMPA, Aldrich) and methyl ethyl ketone (MEK, J. T. Backer) were added to the flask. The temperature was maintained at 75° C. and the reaction was proceeded at 180 rpm for one hour. Then, the temperature was reduced to 50° C. and trethylamine (TEA, RDH) was added to neutralize the reaction for half an hour. After the reaction was completed, double distilled water was added immediately upon reducing the temperature to 45° C. and increasing the rotation speed to 1100 rpm. After water-dispersion, 50 mol % ethylenediamine (EDA, Tedia) were added twice with a 15 minutes gap in between each addition. As a result, waterborne biodegradable polyurethane was produced in the form of emulsion. The ratio of IPDI: marcodiols:DMPA:EDA:TEA of the product was 3.52:1:1: 1.52:1. The synthetic steps are shown in Scheme 1. The soft segments with different prepolymerized temperatures (the rightmost column) are shown in Table 1.

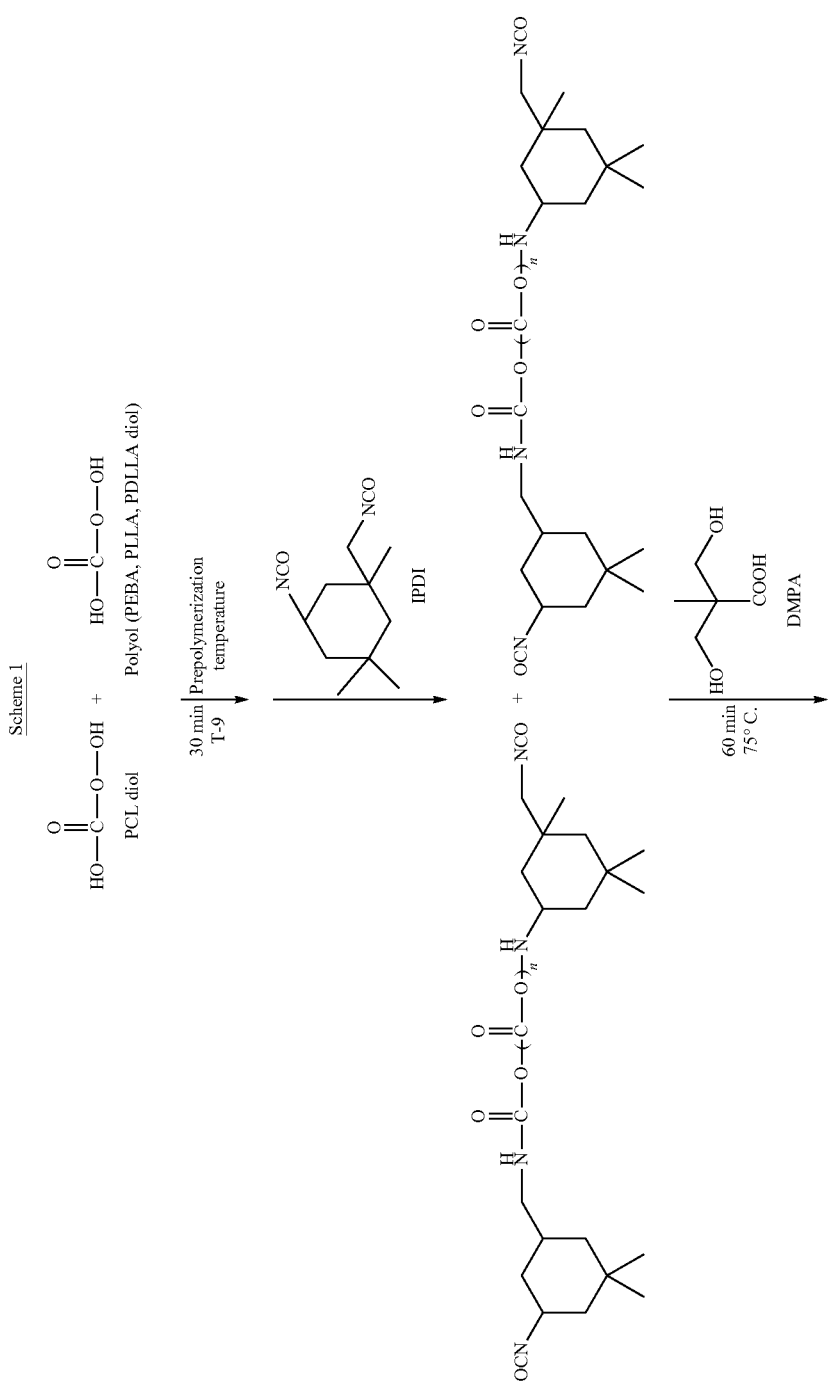

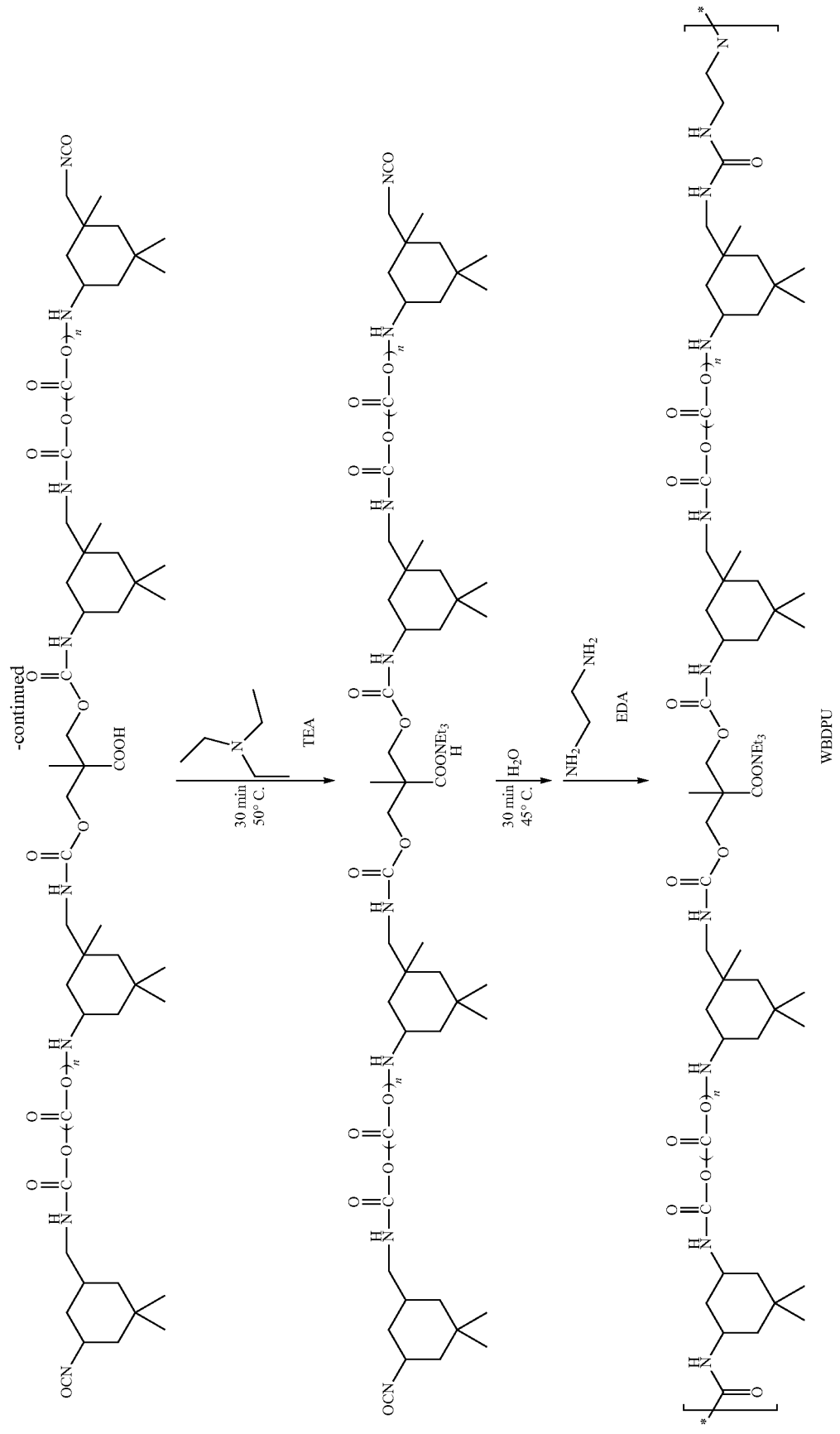

The TEM image of the waterborne biodegradable polyurethane emulsion is shown in FIG. 1. The waterborne biodegradable polyurethane emulsion was analyzed its particle diameter and surface potential. The results indicated that the particle diameter is 39±9 nm and the Zeta Potential is −58±2 mV. The emulsion is also amphiphilic (hydrophilic and hydrophobic) and negatively charged indicating its anticoagulant ability. The emulsion can also be used to stabilize inorganic nanoparticles such as silver nanoparticles and applied to cell uptake or cell tracking.

Figure 2:
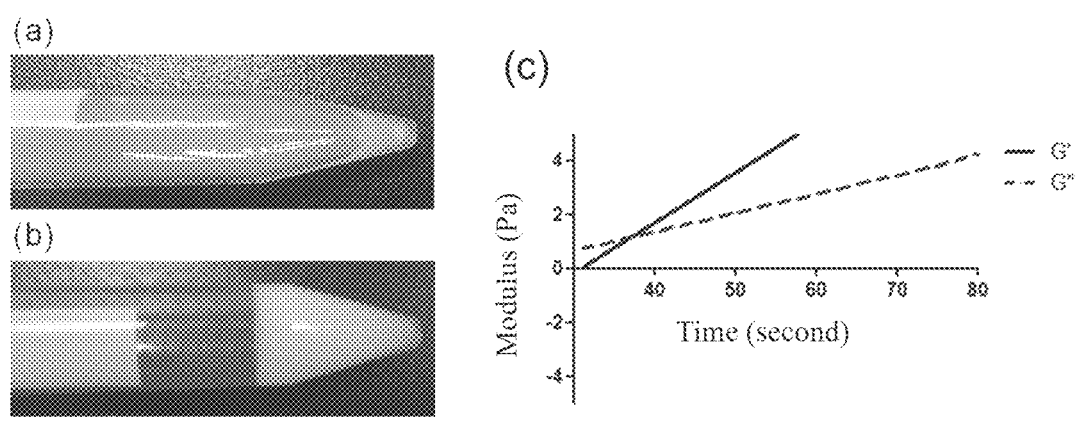
FIGS. 2(a) and (b) are the entitative image of the waterborne biodegradable polyurethane emulsion in low and high temperature; (c) is the Rheology analytical result of the waterborne biodegradable polyurethane emulsion.

Besides, waterborne biodegradable polyurethane emulsion PCL80DL20 can form hydrogel at temperatures higher than 37° C. The entitative image of the waterborne biodegradable polyurethane emulsion in low and high temperature are shown in FIG. 2(a) and FIG. 2(b) and the Rheology analytical result of the waterborne biodegradable polyurethane emulsion is shown in FIG. 2(c). It is shown from the result that the waterborne biodegradable polyurethane emulsion forms hydrogel at approximately 37° C. since G'>G". This characteristic indicates that the waterborne biodegradable polyurethane can be used as drug carrier or gene carrier.

1-3 Membrane Preparation

The 30 wt % waterborne biodegradable polyurethane emulsion was coated onto a glass plate using Spiner at 2300 rpm in 20 seconds. Another appropriate amount of 30 wt % emulsion was placed on Teflon plate and then dried for 72 hours at room temperature (25° C.) and vacuumized for 48 hours at 25° C. in an oven.

Commercial polyurethane (Pellethane 2363-80A, Pellethane, Upjohn) and polylactic acid (PLA, NatureWorks 2002D) were used as control groups in the present embodiment. Pellethane was dissolved in N,N-dimethyl acetamide (DMAc, Tedia) to form a 5 wt % solution. An appropriate amount of the Pellethane solution was place on glass plate, and the glass plate was dried in an oven at 60° C. for 72 hours then vacuumized at 60° C. for 48 hours. Polylactic acid was dissolved in 1,4-dioxane (Tedia) to form a 10 wt % solution. An appropriate amount of the polylactic acid solution was place on Teflon plate and the plate was dried in an oven at 60° C. for 72 hours then vacuumized at 60° C. for 48 hours. Thus, the membrane was produced.

According to the procedure above, soft segment of PCL diol mixed with different proportions of PEBA, soft segment of PCL diol mixed with different proportions of PLLA diol, and soft segment of PCL diol mixed with PDLLA diol can be successfully synthesized into waterborne biodegradable polyurethane and can be prepared in the form of membrane without cracking.

Example 2

Biocompatibility Analysis of the Biodegradable Polyurethane 2-1 Inflammation Test of Macrophage Murine macrophages (J774A.1) from 30 to 40 generations were used in the present embodiment. Oil-based polyurethane (Pellethane, control group) and the waterborne biodegradable polyurethane subjected to subjected to membrane formation and vacuumization were firstly sterilized using 75% ethanol, immersed in phosphate buffered saline (PBS) three times to replace the ethanol, and then place in 24-well corning. The medium used was high glucose Dulbecco's modified Eagle's cell medium (Gibco) containing 10% FBS, 1% PSA, and 1.5 g/L $Na_2CO_3$. Cells were incubated at the density of $2×10^4$ cell/well at the condition of 37° C. and 5% $CO_2$ for 24 hours and 72 hours. Cell morphology was observed using microscope and cell diameter was analyzed using Multisizer™ 3 COULTER COUNTER® (Multisizer 3, Beckman Coulter, USA).

As shown in Table 4, the inflammatory response of the waterborne biodegradable polyurethane was tested using murine macrophage. The waterborne biodegradable polyurethane was made in contact with the cells for 24 hours, and the size difference of cells between the waterborne biodegradable polyurethane and TCPS was above 0.4 μm, while the size difference of cells between the waterborne biodegradable polyurethane and the control group, Pellethane, was above 0.5 μm. When the waterborne biodegradable polyurethane was made in contact with the cells for 72 hours, the size difference of the cells between the waterborne biodegradable polyurethane and TCPS remained to be above 0.4 μm, whereas the size difference of the cells between the waterborne biodegradable polyurethane and the control group increased to be above 0.6 μm. Thus, the biodegradable polyurethane membrane is proofed not to activate murine macrophage and result in inflammatory response.

TABLE 4

Cell sizes of murine macrophage cultured using different materials

| Membrane type | Average cell size (μm) | |
| --- | --- | --- |
|  | 24 hours | 72 hours |
| TCPS | 15.30 ± 0.40 | 15.53 ± 0.36 |
| Pellethane | 15.42 ± 0.25 | 15.76 ± 0.55 |
| PCL100 | 14.90 ± 0.43 | 15.13 ± 0.61 |
| PCL40EB60 | 14.71 ± 0.37 | 15.01 ± 0.46 |
| PCL80LL20 | 14.64 ± 0.33 | 14.89 ± 0.54 |
| PCL80DL20 | 14.64 ± 0.48 | 14.95 ± 0.49 |

2-1-1 Gene Expression of the Murine Macrophage Inflammatory-Related Gene

Cell pellet for analysis was washed twice by PBS. 1 mL of trizol (Intvitrogen, USA) was added to dissolve the cells and 200 μL of chloroform (Tedia) were added to extract RNA. 500 μL of isopropanol (J. T. Backer) were then added to the RNA solution extracted to precipitate RNA. The RNA were collected by centrifugation at 12000 rpm for 15 minutes and washed by 75% EtOH/DEPC solution to replace isopropanol. Finally, RNase-free DEPC-treated water was used to dissolve RNA. The above steps were carried out at 0 to 4° C. and the RNA solution was stored at −20° C. The RNA samples were quantitatively diluted using RNase-free DEPC-treated water and the concentration of RNA was determined by the absorbance of 260 nm and 280 nm measured using visible light/ultra violet light spectrometer (U-2000, Hitachi).

Reverse transcription was performed by using RevertAid™ First Strand cDNA Synthesis kit (Fermentas, USA). 0.1 to 0.5 μg of RNA were used according to the quantitative result, and 1 μL of oligo dT were added. RNase-free DEPC-treated water was then added to make the volume up to a total of 12 μL. After reacting at 70° C. for 5 minutes, 4 μL of 5× reaction buffer solution, 1 μL of RiboLock Ribonuclease inhibitor, and 2 μL of 10 mM dNTP were added. After reaction at 37° C. for 5 minutes, 1 μL of RTase were added. Then, reaction was carried out at 42° C. for 60 minutes, and furthermore, at 70° C. for 10 minutes to produce cDNA.

2 μL of 5×PCR Maister, 1 μL of template DNA 1, 1 μL of forward primer, 1 μL of reverse primer, and 17 μL of sterilized deionized water were loaded in 0.2 mL microtube. Thermal cycle (GeneAmp® PCR system 2700, AB, USA) was used. Gene primers were designed as follow: murine IL-1 (forward): CCCAAGCAATACCCAAAGAAGAAG (SEQ ID NO: 1); murine IL-1 (reverse): TGTCCTGAC-CACTGTTGTTTCC (SEQ ID NO: 2); murine IL-6 (forward): TTCCATCCAGTTGCCTTCTTG (SEQ ID NO: 3); murine IL-6 (reverse): TCATTTCCACGATTTCCCAGAG (SEQ ID NO:4); murine TNF-α (forward): CGAGT-GACAAGCCTGTAGCC (SEQ ID NO: 5); murine TNF-α-32-(reverse): TTGAAGAGAACCTGGGAGTAGAC (SEQ ID NO: 6); murine β-actin (forward): TCCTGTGGCATC-CACGAAACT (SEQ ID NO: 7); murine β-actin (reverse): GGAGCAATGATCCTGATCTTC (SEQ ID NO: 8); bovine eNOS (forward): TAGAATTCCCAGCAC-CTTTGGGAATGGCGAT (SEQ ID NO: 9); bovine eNOS (reverse): ATAGAATTGGATTCACTTCTGTGTTGCTG-GACTCCTT (SEQ ID NO: 10); bovine β-actin (forward): AAAGACAGCTATGTGGGAGA (SEQ ID NO: 11); bovine β-actin (reverse): ATGATCTGGGTCATCTTCT (SEQ ID NO: 12). The annealing temperature was set at 55° C. and automated capillary nucleic acid analyzer (eGene, HAD-GT12TM) was used to access the measurement of gene expression.

Capillary electrophoresis was carried out according to the above reverse-transcription polymerase chain reaction to isolate the four sets of genes of β-actin, IL-1 (interlukin-1), IL-6 (interlukin-6), and TNF-α. Data measured were divided by half the quantitative gene expression of normal distribution in the cells to give the immunoassay results.

Figure 3:
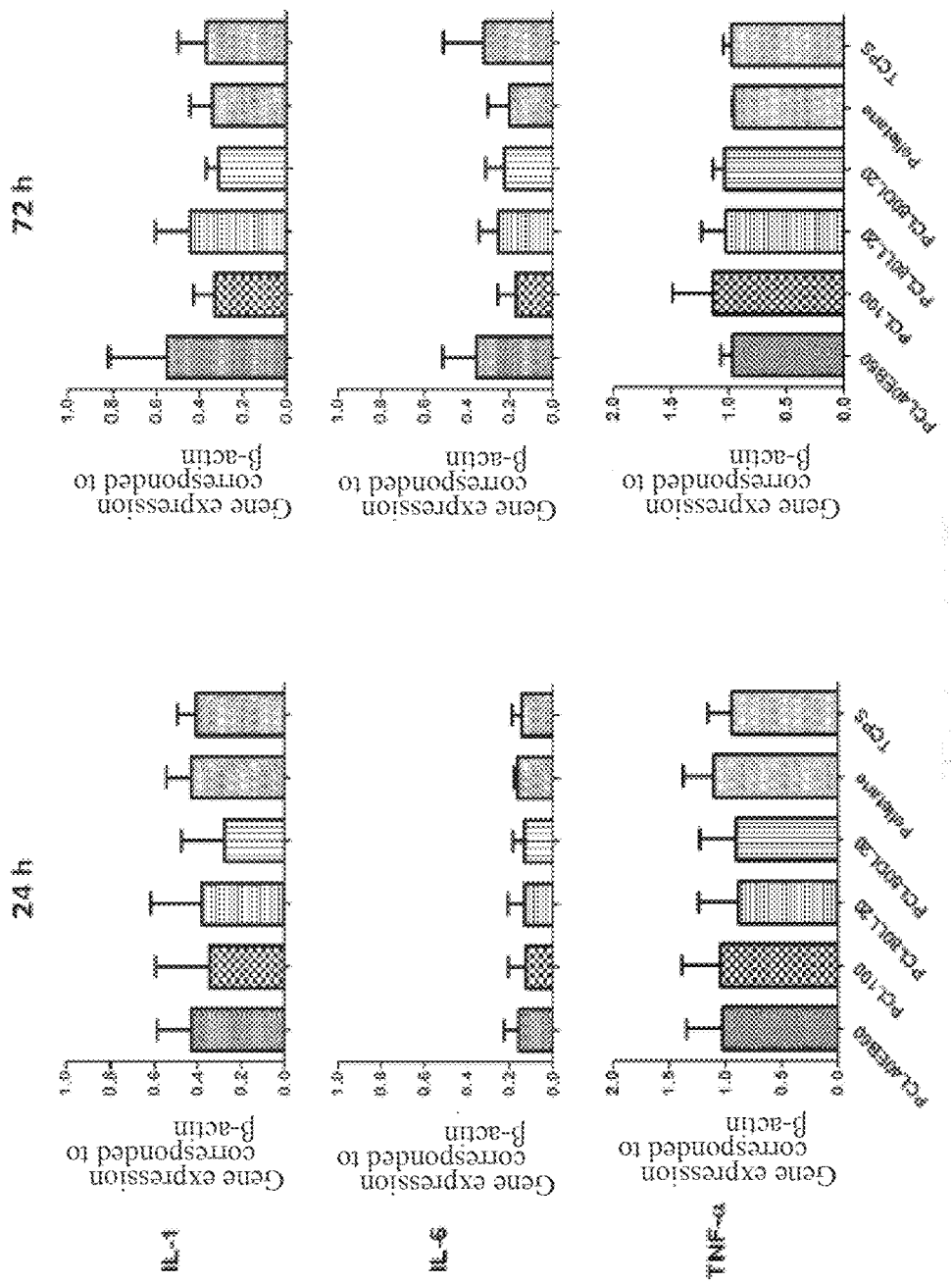
FIG. 3 is the inflammatory test of murine macrophage using different waterborne biodegradable polyurethane.

FIG. 3 indicates the influence of different materials to murine macrophage inflammatory-related gene expression. At 24 hours, comparing with TCPS and Pellethane, the waterborne biodegradable polyurethane exhibits no significant difference regarding Interleukin-1 (IL-1), Interleukin-6 (IL-6), and Tumor necrosis factor-alpha (TNF-α). At 72 hours, although slight increases are observed with waterborne biodegradable polyurethane treated IL-1, IL-6, and TNF-α, the difference is still not significant comparing with TCPS. Hence, the waterborne biodegradable polyurethane of the present invention is proof not to trigger significant inflammatory response.

2-2 In Vitro Degradability Test

The waterborne biodegradable polyurethane subjected to membrane formation and vacuumization was cut into square (5 mm×5 mm) according to the regulation of ISO 10993-13 and immersed in pH 7.4 phosphate buffered saline (PBS). The value of solution value over surface area was adjusted to within the range of 1 to 6 cc/mm$^2$ and the solution was placed in oven with constant temperature of 50° C. After 7, 14, 21, and 28 days, the waterborne biodegradable polyurethane was collected and the surface was washed using double-distilled water. The washed waterborne biodegradable polyurethane was then placed in oven to dry for 24 hours at 50° C. following vacuumization for another 24 hours. The weights of the waterborne biodegradable polyurethane before and after the experiment were measured and the remaining percentage by weight was calculated according to Formula 1.

The waterborne biodegradable polyurethane subjected to membrane formation and vacuumization was cut into square (1 cm×1 cm) and immersed in 3 wt % sodium hydroxide (NaOH) and placed in oven with a constant temperature of 37° C. After 4, 8, 12, and 24 hours, the waterborne biodegradable polyurethane was collected and the surface was washed using double-distilled water. The washed waterborne biodegradable polyurethane was then placed in oven to dry for 24 hours at 37° C. following vacuumization for another 24 hours. The weights of the waterborne biodegradable polyurethane before and after the experiment were measured and the remaining percentage by weight was calculated according to Formula 1.

$$\text{Remaining percentage by weight (\%)} = Wt/Wo \times 100\% \quad \text{Formula 1}$$

Wo is the starting weight (g); Wt is the washed and dried weight after degradation On the other hand, polycaprolactone diol and polyethylene butylene adipate diol in the ratio of 60:40 and 80:20, as well as polycaprolactone diol and poly-L-lactide diol in the ratio of 40:60 and 60:40 were made into waterborne biodegradable polyurethane respectively according to the same method disclosed above for comparison.

Figure 4:
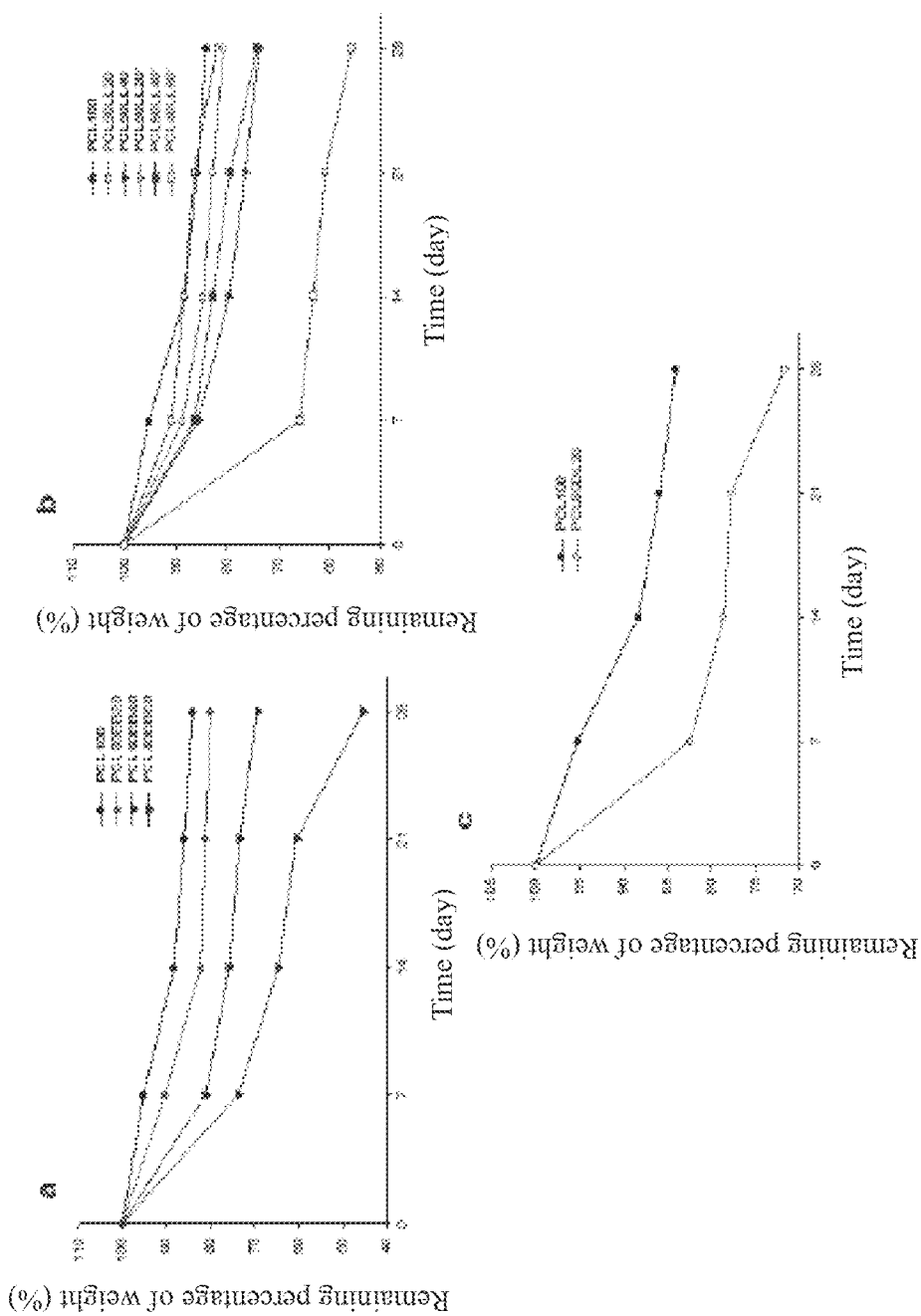
FIG. 4 is the relationship of the remaining percentage of weight of the waterborne biodegradable polyurethane under the accelerated degradation by PBS at 50° C., wherein (a) indicates soft segment consisting of PCL diol and PEBA diol; (b) indicates soft segment consisting of PCL diol and PLLA diol; (c) indicates soft segment consisting of PCL diol and PDLLA diol.
Figure 5:
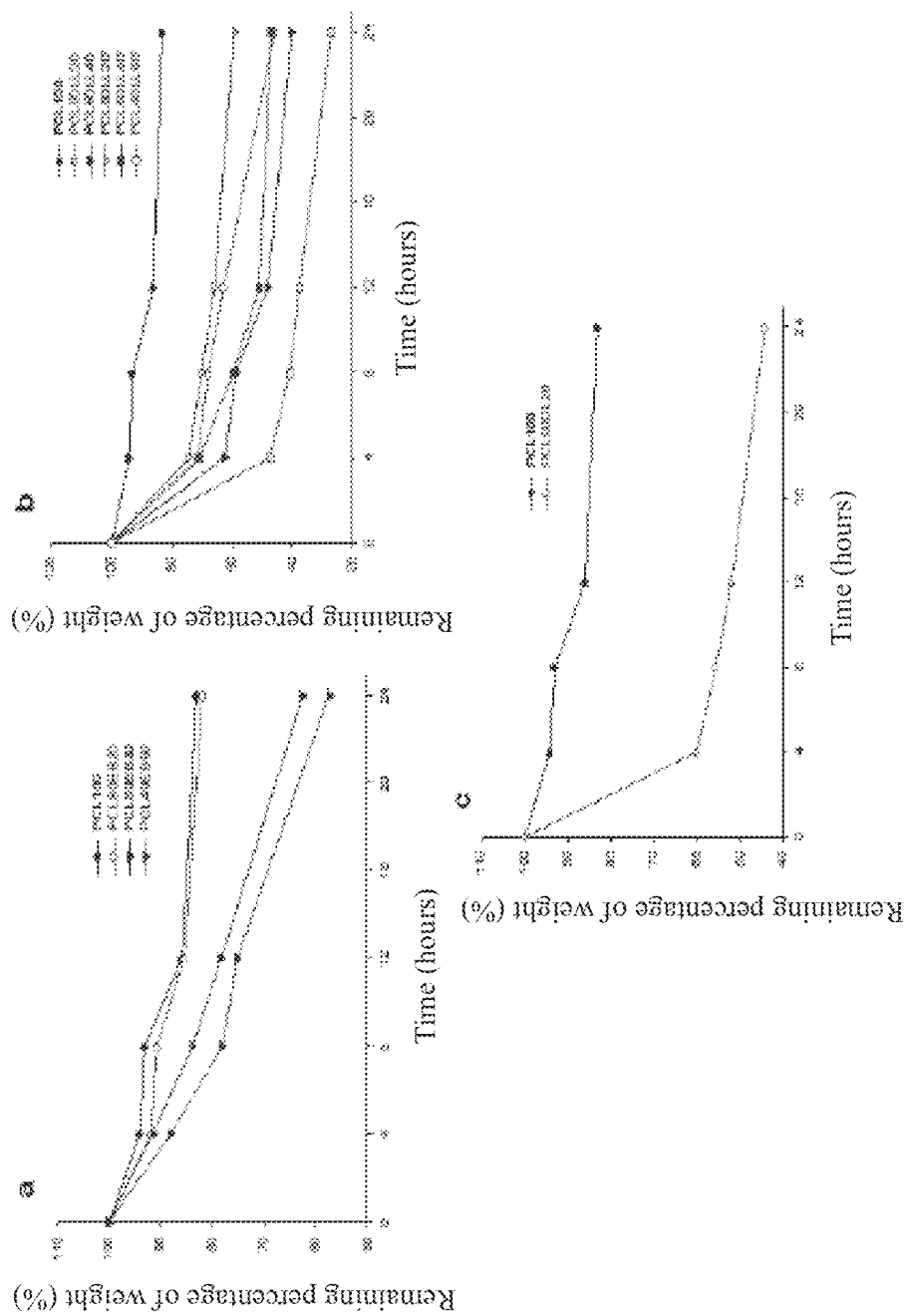
FIG. 5 is the relationship of the remaining percentage of weight of the waterborne biodegradable polyurethane under the accelerated degradation by NaOH at 37° C., wherein (a) indicates soft segment consisting of PCL diol and PEBA diol; (b) indicates soft segment consisting of PCL diol and PLLA diol; (c) indicates soft segment consisting of PCL diol and PDLLA diol.

The accelerated degradation test of the waterborne biodegradable polyurethane with PBS at 50° C. is shown in FIG. 4. The higher the proportion of PEBA diol, the faster the degradation rate of the waterborne biodegradable polyurethane when the soft segment was made of PCL diol and PEBA diol, which results in a remaining weight percentage between 84 to 45 wt % after 28 days. The higher the proportion of PLLA diol, the faster the degradation rate of the waterborne biodegradable polyurethane when the soft segment was made of PCL diol and PLLA diol, which results in a remaining weight percentage between 84 to 55 wt % after 28 days. The higher the proportion of PDLLA diol, the faster the degradation rate of the waterborne biodegradable polyurethane when the soft segment was made of PCL diol and PDLLA diol, which results in a remaining weight percentage between 84 to 71 wt % after 28 days. In addition, the accelerated degradation test of the waterborne biodegradable polyurethane with 3 wt % NaOH is shown in FIG. 5. The higher the proportion of PEBA diol, the faster the degradation rate of the waterborne biodegradable polyurethane when the soft segment was made of PCL diol and PEBA diol, which results in a remaining weight percentage between 83 to 57 wt % after 24 hours. The higher the proportion of PLLA diol, the faster the degradation rate of the waterborne biodegradable polyurethane when the soft segment was made of PCL diol and PLLA diol, which results in a remaining weight percentage between 83 to 26 wt % after 24 hours. The higher the proportion of PDLLA diol, the faster the degradation rate of the waterborne biodegradable polyurethane when the soft segment was made of PCL diol and PDLLA diol, which results in a remaining weight percentage between 83 to 44 wt % after 24 hours.

The in vitro degradation rates of soft segments made of PCL diol and PEBA diol in PBS and NaOH are rated as follow: PCL40EB60>PCL60EB40>PCL80EB20>PCL100. The in vitro degradation rates of soft segments made of PCL diol and PLLA diol in PBS and NaOH are rated as follow: PCL40LL60>PCL60LL40>PCL80LL20>PCL100. The in vitro degradation rates of soft segments made of PCL diol and PDLLA diol in PBS and NaOH are rated as follow: PCL80DL20>PCL60LL40>PCL80LL20>PCL100.

2-3 Degradability Test of Murine Subcutaneous Implantation

The waterborne biodegradable polyurethane subjected to membrane formation and vacuumization was cut into square (10 mm×10 mm×0.2 mm), sterilized by 75% ethanol, and then immersed in PBS three times to replace the ethanol. After gas anesthesia, 10 mm×10 mm subcutaneous incisions were done on both side of the spine of adult Sprague-Dawley (SD) rat and the waterborne biodegradable polyurethane membrane of the present invention was implanted. After carbon dioxide euthanasia after 29 days, the implanted waterborne biodegradable polyurethane membrane was collected, washed by double-distilled water, and vacuumed for 24 hours. The weights of the waterborne biodegradable polyurethane membrane before and after implantation were measured and the remaining percentage of weight was calculated according to Formula 1. The molecular weights of the waterborne biodegradable polyurethane membrane before and after implantation were measured using gel permeation chromatography (GPC, Waters apparatus) and the remaining percentage of molecular weight was calculated according to Formula 2. In addition, Scanning Electron Microscope (SEM, Hitachi S-4800) was used to observe the surface changes of the waterborne biodegradable polyurethane membrane before and after implantation.

Remaining percentage of molecular weight (%)=$Mt/Mo$×100%     Formula 2

Figure 6:
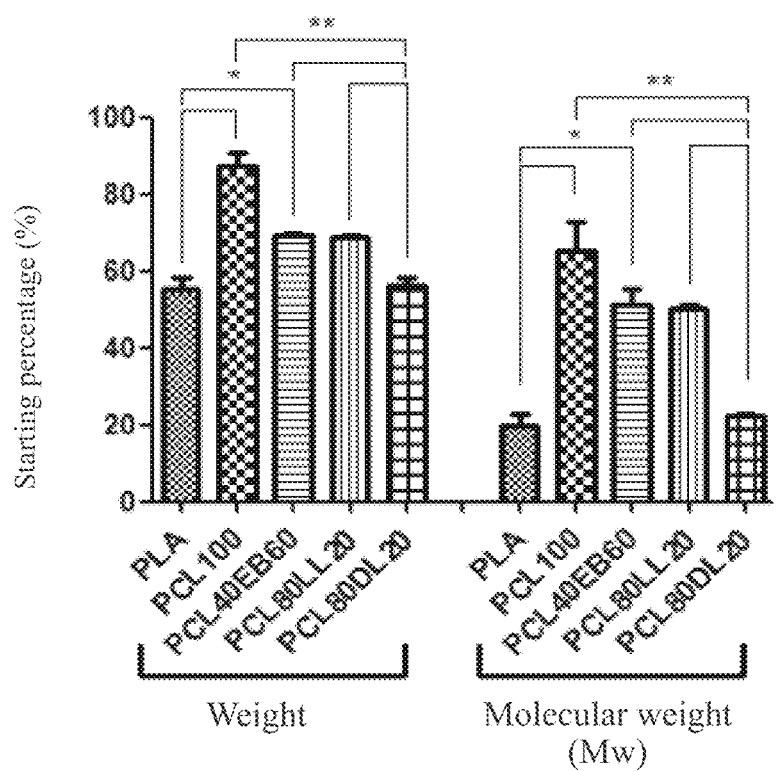
FIG. 6 is the remaining percentage of weight and the remaining percentage of molecular weight before and after implantation. (*$p<0.05$; **$p<0.05$)

Mo is the starting molecular weight (Mw); Mt is the washed and dried molecular weight after degradation After 29 days of murine subcutaneous implantation, small pores can be seen on the surface of the waterborne biodegradable polyurethane and the diameter of the pores seen on the PLA surface is approximately 5 μm. PCL80DL20 generates more pores during in vivo degradation. Please refer to FIG. 6 for the remaining percentage of weight and the remaining percentage of molecular weight before and after implantation. The least remaining percentage of weight measured are PLA (55.25%) and PCL80DL20 (56.03%) indicating the fastest degradation, whereas the higher remaining percentage of weight measured is PCL 100 (85.66%) indicating a slower degradation. Regarding the remaining percentage of molecular weight before and after implantation, the remaining percentage of molecular weight of PLA (19.84%) is the least, the remaining percentage of molecular weight of PCL80DL20 (22.13%) is slight higher, and the remaining percentage of molecular weight of PCL100 (65.27%) is the highest, indicating the slowest degradation rate. The in vivo degradation rate is rated as follow:
PLA≥PCL80DL20>PCL40EB60≥PCL80LL20>PCL100.

Example 3

Preparation of Scaffold 3-1 Scaffold Preparation by Electrospinning

An electrospinning device was constructed by using high voltage power supplier (YSTC), syringe pump (KDS-100, KD Scientific, USC), and spinneret (20G, TERUMO). The waterborne biodegradable polyurethane subjected to membrane formation was dissolved in acetone (Tedia) to prepare 10 to 25 wt % solution and loaded into the syringe pump. The high voltage power supplier was attached with one end to the spinneret and the other to the collector. The flow speed of the syringe and the voltage were set at 10 to 17 μL/min and 7 to 9 kV, respectively. A layer of aluminum foil or glass plate could be placed on the collector to allow the operating distance between the tip of the spinneret and the collector to be 19 cm. The electrospinning nano/micro fiber could then be collected on the aluminum foil or glass plate and followed by vacuumization at 25° C. for 48 hours. On the other hand, poly(D,L-lactide) (molecular weight=121140 Da, low crystalline, Ingeo 2002D, NatureWorks) was dissolved in cosolvent, acetone (Tedia) and 1,4-dioxane (Tedia) and loaded into the syringe. For collecting electrospinning fiber, the flow speed, voltage, and operating distance between the tip of the spinneret and the collector were set at 10 μL/min, 9 kV, and 19 cm, respectively. Detailed parameters of the electrospinning fiber are shown in Table 5.

TABLE 5

Parameters of the electrospinning fiber

| Sample | Biodegradable polyurethane (wt %) | Acetone (wt %) | 1,4-dioxane (wt %) | Voltage (kV) | Flow speed (μL/min) | Operating distance (cm) |
|---|---|---|---|---|---|---|
| PCL100 | 10 | 90 | — | 7.1 | 15 | 19 |
| PCL40EB60 | 18 | 82 | — | 7.1 | 10 | 19 |
| PCL80LL20 | 10 | 90 | — | 7.1 | 15 | 19 |
| PCL80DL20 | 25 | 75 | — | 7.1 | 17 | 19 |
| PLA | 10 | 36 | 54 | 9.0 | 10 | 19 |

Figure 7:
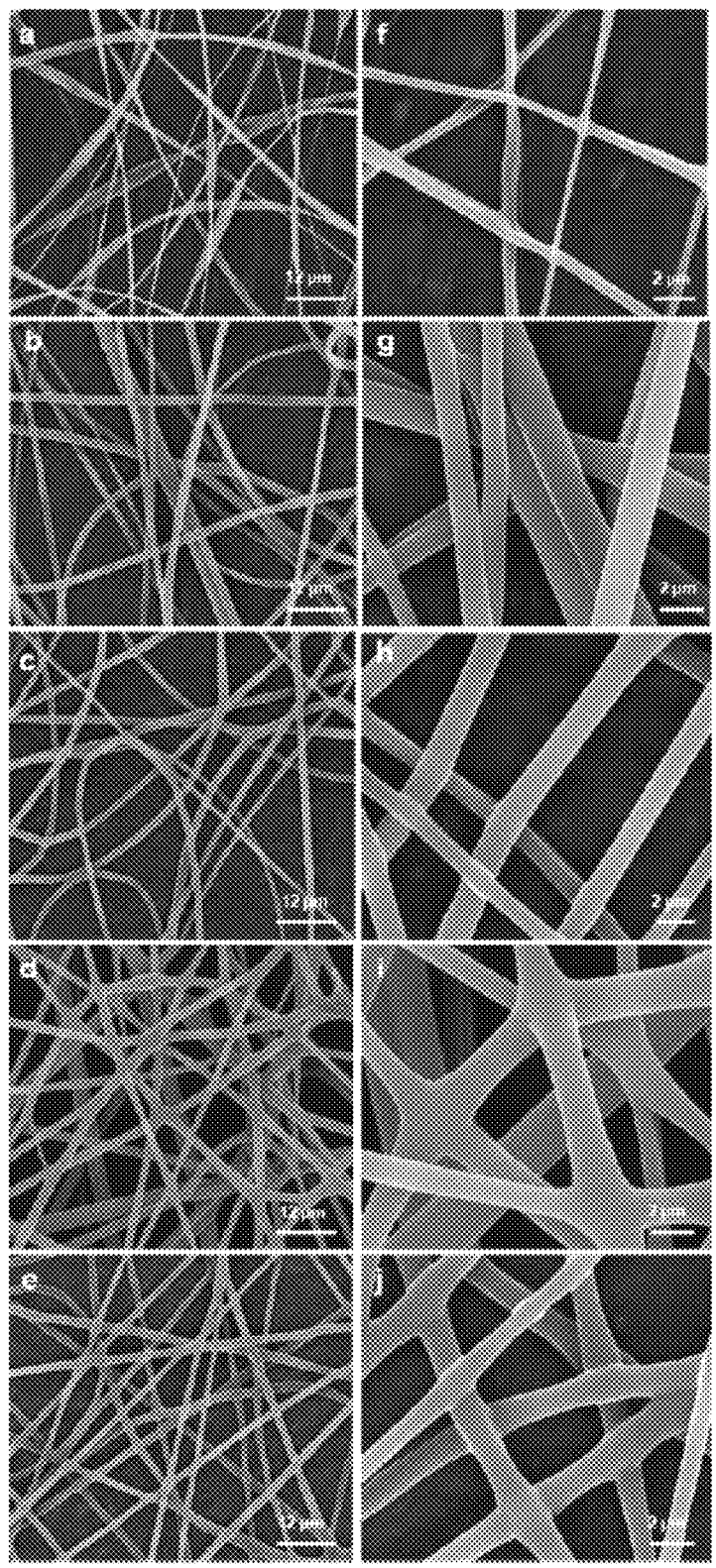
FIG. 7 is the surface configuration of electrospinning fibers, wherein (a, indicate $PLA^e$; (b, g) indicate $PCL100^e$; (c, h) indicate $PCL40EB60^e$; (d, i) indicate $PCL80LL20^e$; (e, j) indicate $PCL80DL20^e$.

The electrospinning fiber obtained by macromolecular solution containing waterborne biodegradable polyurethane, acetone and polylactic acid, acetone, and 1,4-dioxane under conditions of 10 to 17 μL/min in flow speed and 7 to 9 kV in voltage is shown in FIG. 7 in which the electrospinning fiber is thin and fibrous without any occurrence of beads. The diameter of PCL100$^e$/acetone (10/90 wt %) is 1.57±0.35 μm; the diameter of PCL40EB60$^e$/acetone (18/82 wt %) is 1.40±0.38 μm; the diameter of PCL80LL20$^e$/acetone (10/90 wt %) is 1.70±0.36 μm; the diameter of PCL80DL20$^e$/acetone (25/75 wt %) is 1.42±0.21 μm; the diameter of PLA$^e$/acetone/1,4-dixane (10/36/54 wt %) is 1.24±0.66 μm.

Moreover, nano fiber with 457.5±44.7 μm in diameter can be fabricated by incorporating polyethylene oxide (PEO) into waterborne biodegradable polyurethane emulsion and undergoing electrospinning directly.

3-2 Scaffold Preparation by Freeze Drying 3-2-1 Preparation by Freeze Drying 10 mL of 30 wt % waterborne biodegradable polyurethane emulsion was placed onto Teflon plate and froze at −20° C. for 24 hours. Then a membrane with thickness of 2 to 3 mm was obtained after freeze drying using freeze dryer (FDU-1200, Eyela, Japan) for 24 hours.

Figure 8:
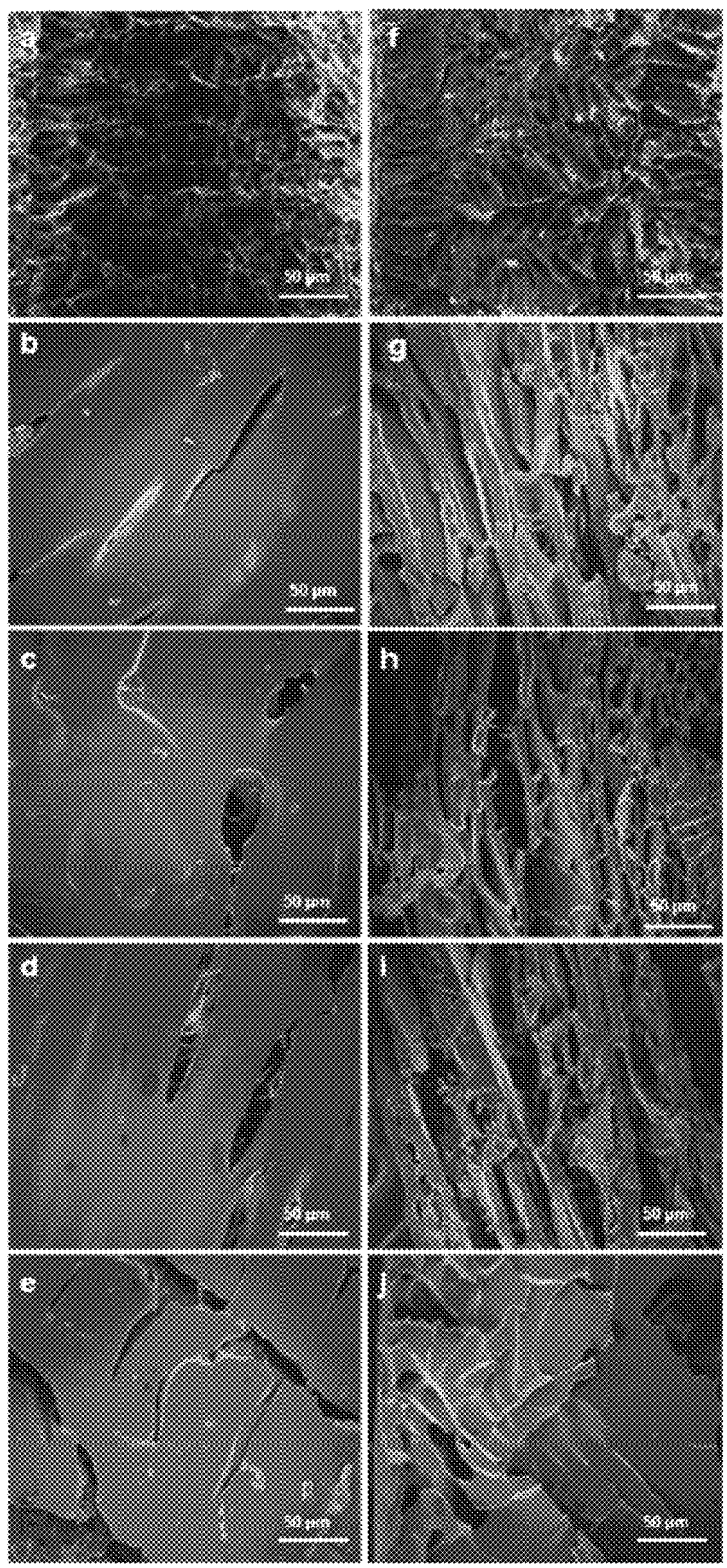
FIG. 8 is the surface configuration of membrane freeze dried at −20° C., wherein (a, f) indicate $PLA^f$; (b, g) indicate $PCL100^f$; (c, h) indicate $PCL40EB60^f$; (d, i) indicate $PCL80LL20^f$; (e, j) indicate $PCL80DL20^f$; (a, b, c, d, e) indicate the surface configuration and (f, g, h, i, j) indicate the cross-section configuration.

The structures of the surface and cross-section of the membrane formed are shown in FIG. 8. For PCL100$^f$ freeze dried membrane, the diameter of the pore on the surface is 8.04±2.24 μm and the diameter of the pore on the cross-section is 52.05±19.28 μm; for PCL40EB60$^f$ freeze dried membrane, the diameter of the pore on the surface is 12.74±4.06 μm and the diameter of the pore on the cross-section is 38.51±16.63 μm; for PCL80LL20$^f$ freeze dried membrane, the diameter of the pore on the surface is 8.86±3.99 μm and the diameter of the pore on the cross-section is 48.61±20.33 μm; for PCL80DL20$^f$ freeze dried membrane, the diameter of the pore on the surface is 25.91±9.04 μm and the diameter of the pore on the cross-section is 53.70±25.25 μm; for PLA$^f$ freeze dried membrane, the diameter of the pore on the surface is 49.45±9.04 μm and the diameter of the pore on the cross-section is 65.48±10.42 μm. It is shown that the diameters of the pores on the surface and the cross-section are mostly within the range of the diameter of vascular graft endothelialization.

Figure 9:
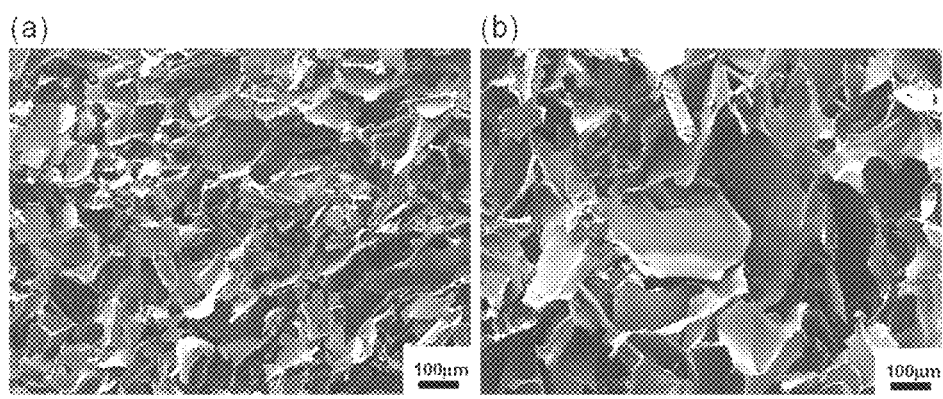
FIG. 9 is the SEM image of the foams of waterborne biodegradable polyurethane emulsion formed by 10% dilution and freeze drying, where (a) is the top view and (b) is the bottom view.

In addition, foams (as shown in FIG. 9) are formed by diluting the waterborne biodegradable polyurethane emulsion followed by freeze drying procedure. The pores of the foam are larger and more abundant and are distributed in an asymmetrical manner. The mechanical strength is regardless of dilution, however, with diluted waterborne biodegradable polyurethane emulsion, the flexibility is better.

3-2-2 Preparation by Particle-Leaching Method and Freeze Drying

Additionally, particle-leaching method was applied. Waterborne biodegradable polyurethane and PLA (Mw=121.4 kDa, low crystalline, Ingeo 2002D, NatureWorks) subjected to membrane formation were separately dissolved using solvent, 1,4-dioxane (Tedia) to form homogenous macromolecular solution of PLA/1,4-dioxane (5/95 wt %). Firstly, glucose source was vacuumized for 12 hours at 60° C. using a vacuum oven in a sealed heating environment. Then further vacuumized at 22 to 25° C. for 12 hours. Two sieves (ASTM E 11-79 No. 50 and 140) were used to select glucose particle of 100 to 300 μm in diameter to serve as porogen under condition of below 20% RH. 2 mL of the solution were placed into a cylinder container (diameter=20 mm; thickness=10 mm) having 2 g of sugar particle (D(+)-glucose anhydrous, Showa, particle diameter=100 to 300 μm) for 30 minutes, then froze at −20° C. for 24 hours. After further freeze dried for 24 hours using freeze dryer (FDU-1200, Eyela, Japan), samples (diameter=20 mm; thickness=5 mm) were taken from the cylinder container and immersed in water for 24 hours. The water was renewed every 30 minutes during the process. After the sugar particle and the remaining solvent were fully dissolved in water, samples were taken from the water and then freeze dried again for 24 hours using freeze dryer to yield samples of 3 to 4 mm in thickness. Samples were further cut into cylinder with a diameter of 15 mm using casting knife (diameter=15 mm)

Figure 10:
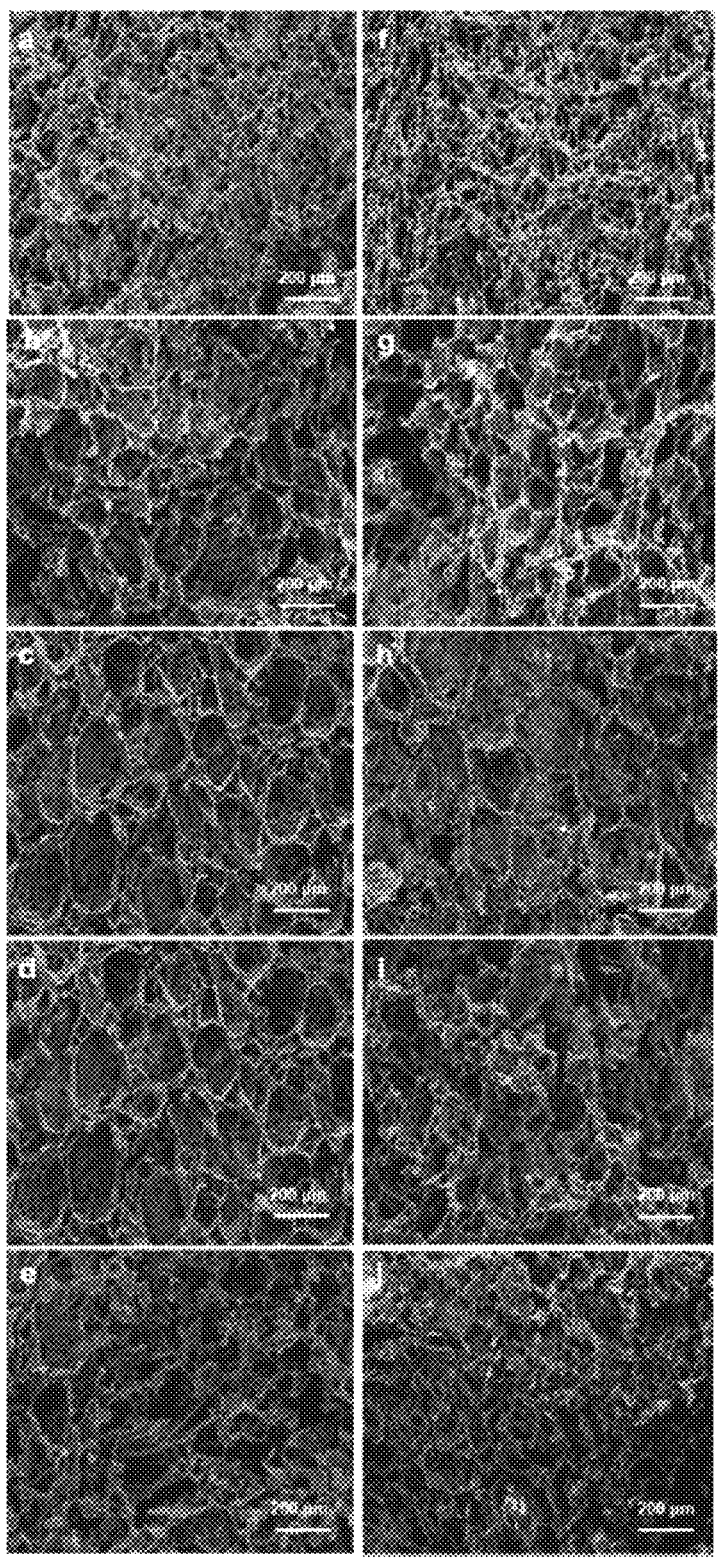
FIG. 10 is the surface configuration of scaffold obtained by using glucose in particle-leaching and freeze drying at −20° C., wherein (a, f) indicate $PLA^s$; (b, g) indicate $PCL100^s$; (c, h) indicate $PCL40EB60^s$; (d, i) indicate $PCL80LL20^s$; (e, j) indicate $PCL80DL20^s$; (a, b, c, d, e) indicate the surface configuration and (f, g, h, j) indicate the cross-section configuration.

The structures of the surface and cross-section are shown in FIG. 10. For PCL100$^s$ freeze dried scaffold, the diameter of the pore on the surface is 160.25±7.49 μm and the diameter of the pore on the cross-section is 139.08±14.75 μm; for PCL40EB60$^s$ freeze dried scaffold, the diameter of the pore on the surface is 171.79±20.92 μm and the diameter of the pore on the cross-section is 186.68±29.27 μm; for PCL80LL20$^s$ freeze dried scaffold, the diameter of the pore on the surface is 207.06±18.04 μm and the diameter of the pore on the cross-section is 152.82±20.46 μm; for PCL80DL20$^s$ freeze dried scaffold, the diameter of the pore on the surface is 162.68±4.17 μm and the diameter of the pore on the cross-section is 149.60±11.71 μm; for PLA$^s$ freeze dried scaffold as the control group, the diameter of the pore on the surface is 147.25±13.79 μm and the diameter of the pore on the cross-section is 147.22±10.23 μm. It is shown that the diameters of the pores on the surface and the cross-section are also mostly within the range of the diameter of vascular graft endothelialization.

3-3 Mechanical Properties of the Membrane

Different waterborne biodegradable polyurethane membranes subjected to membrane formation were cut into dumb-bell shape using standard mold (length=20 mm; width=1 mm) For measuring the thickness of the samples, firstly, both edges of the samples were clamped tightly using fixing clamps, then tensile test was carried out at a constant elongation speed set at 100 mm/min using universal tension machine (HT-8504, HungTa). According to stress-strain diagram, the Young's modulus, tensile strength, and elongation could be determined to compare the physical strength of each material.

The Young's modulus of the waterborne biodegradable polyurethane is between 0.5 to 40 MPa, while the tensile strength of the waterborne biodegradable polyurethane is between 5 to 50 MPa. The tensile strength of the pore-less membrane is greater than 400%, while the tensile strength of the porous membrane is greater than 220%. Preferred data of waterborne biodegradable polyurethane are shown in Table 6.

TABLE 6

| Sample | Young's modulus (MPa) | 100% Modulus (MPa) | Tensile strength (MPa) | Elongation (%) |
| --- | --- | --- | --- | --- |
| PCL100 | 30.9 ± 7.9 | 5.3 ± 0.1 | 34.9 ± 3.1 | 535.5 ± 19.7 |
| PCL40EB60 | 29.9 ± 1.9 | 4.6 ± 0.3 | 25.7 ± 5.3 | 517.2 ± 10.8 |
| PCL80LL20 | 23.2 ± 1.6 | 6.2 ± 0.3 | 28.0 ± 3.4 | 581.1 ± 4.2 |
| PCL80DL20 | 4.6 ± 0.7 | 3.8 ± 0.2 | 12.6 ± 3.9 | 655.5 ± 17.5 |
| PCL100$^f$ | 5.6 ± 0.9 | 1.6 ± 0.4 | 2.2 ± 0.8 | 222.0 ± 25.6 |
| PCL40EB60$^f$ | 5.0 ± 0.7 | 1.4 ± 0.2 | 2.9 ± 0.2 | 279.0 ± 14.8 |
| PCL80LL20$^f$ | 8.6 ± 0.4 | 2.4 ± 0.3 | 3.8 ± 0.3 | 279.8 ± 5.8 |
| PCL80DL20$^f$ | 1.5 ± 0.4 | 1.6 ± 0.4 | 2.5 ± 0.5 | 287.8 ± 26.4 |

The waterborne biodegradable polyurethane with soft segment made of PCL diol and PEBA diol, represented as PCL60EB40, exhibits Young's modulus between 24.3 to 33.4 MPa, tensile strength between 25.7 to 34.9, and elongation between 512.7 to 537.4%. The Young's modulus and tensile strength decreases with the increase of PEBA diol proportion, while the elongation shows no significant changes.

The waterborne biodegradable polyurethane with soft segment made of PCl diol and PLLA diol exhibits Young's modulus between 23.20 to 131.50 MPa, tensile strength between 11.0 to 34.9 MPa, and elongation between 190.0 to 581.1%. With the increase of PLLA diol proportion under a prepolymerization temperature of 95° C., Young's modulus shows a tendency to decrease and then increase, while tensile strength decreases significantly. Elongation, on the other hand, shows a tendency to increase and then decrease.

The waterborne biodegradable polyurethane with soft segment made of PCL diol and PDLLA diol exhibits Young's modulus between 4.6 to 31.0 MPa, tensile strength between 12.6 to 34.9 MPa, and elongation between 535.5 to 655.5%. With the increase of PDLLA diol proportion, Young's modulus and tensile strength decrease significantly, whereas elongation shows a significant increase. Overall, PCL100, PCL40EB60, PCL80LL20, and PC180DL20 are the preferred elastomer having mechanical properties.

As shown in Table 6, freeze dried membrane exhibits Young's modulus between 1.5 to 8.6 MPa, tensile strength between 2.2 to 3.8 MPa, and elongation between 220.0 and 287.8%. Scaffold prepared by directly freeze drying the waterborne biodegradable polyurethane exhibits a great margin of decrease regarding all Young's modulus, tensile strength, and elongation comparing to membrane dried in room temperature.

3-4 Scaffold Surface Modification

The freeze dried waterborne biodegradable polyurethane membrane and a polylactic acid membrane were used. Sulfonated chitosan (Mw=140 kDA, deacetylation degree=95%, sulfonation degree=99%) was grafted using atmospheric-pressure plasma (San Fang Machinery Co., Ltd., Model Type: FH3001+HTR1001+RD1004) with air mixture of 20% oxygen and 80% nitrogen and inlet pressure of 2.5 kg/cm$^2$. The height of nozzle and the speed of platform movement were set at 20 mm and 15 m/min, respectively. After scanning by atmospheric-pressure plasma, biological solution of chitosan derivatives (2 wt %) were quickly coated onto the membrane to allow reaction to take place for 30 minutes, then the membrane was washed by double-distlled water and dried. The surface characteristics after grafting were analyzed by contact angle (FTA- 1000B, First Ten Angstrom Company, USA), Attenuated Total Reflection Fourier Infrared Spectroscopy (spectrum 100 model, Perkin Elmer), and Scanning Electronic Microscopy (JEOL-JSM-7600).

Figure 11:
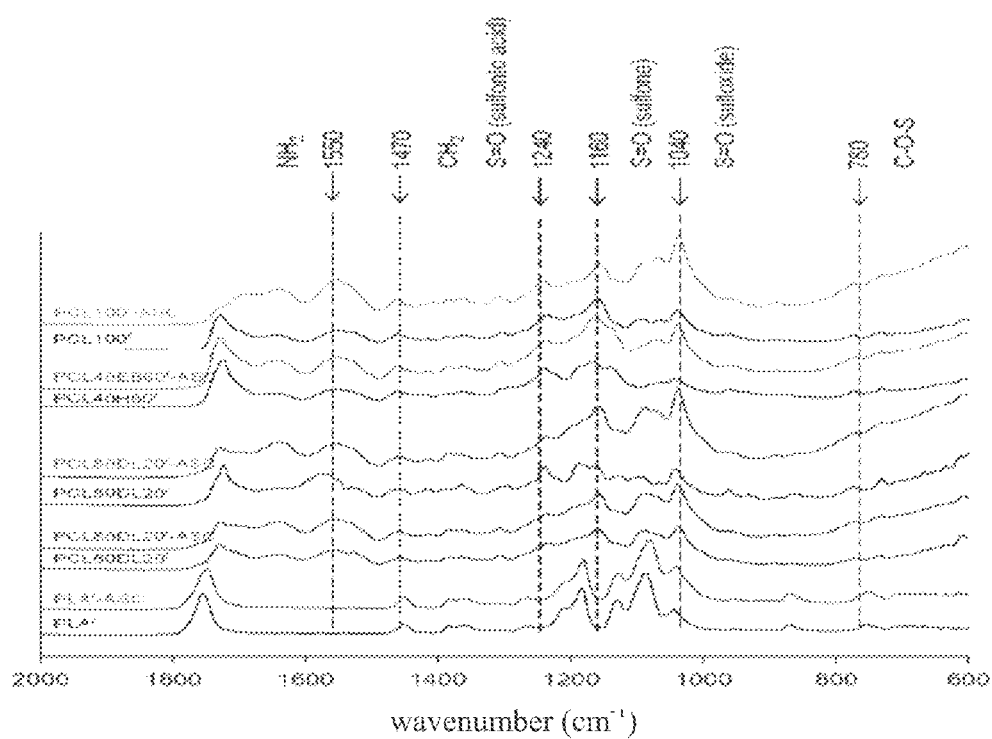
FIG. 11 is the analytical results of freeze dried membrane with surface modification by sulfonated chitosan using Attenuated Total Reflection Fourier Infrared Spectroscopy.

As shown in FIG. 11, the peak absorption of the freeze dried waterborne biodegradable polyurethane membrane is 1550 cm$^{-1}$ for $NH_2$, 1470 cm$^{-1}$ for $CH_2$, 1240 cm$^{-1}$ for S=O (sulfonic acid), 1160 cm$^{-1}$ for S=O (sulfone), 1040 cm$^{-1}$ for S=O (sulfoxide), and 780 cm$^{-1}$ for C—O—S, whereas the peak absorption of the freeze dried polylactic acid membrane is 1040 cm$^{-1}$ for S=O (sulfoxide) with a significant increase in absorption peak intensity. On the other hand, regarding the contact angle, PCL100 with surface modified by sulfonated chitosan decreases to 53.7±1.5°, PCL40EB60 with surface modified by sulfonated chitosan decreases to 54.4±3.5°, PCL80LL20 with surface modified by sulfonated chitosan decreases to 57.2±2.5°, PCL80DL20 with surface modified by sulfonated chitosan increases to 52.1±2.1°, and PLA with surface modified by sulfonated chitosan decreases significantly to 48.3±3.6°. Hence, it is proofed that sulfonated chitosan can be successfully grafted on to the surface of the freeze dried waterborne polyurethane membrane of the present invention.

Example 4

Biocompatibility Test of the Scaffold 4-1 Adhesion and Proliferation of Endothelial Cells Bovine carotid artery endothelial cells (BEC) from 9 to 15 generations were used. All waterborne biodegradable polyurethane electrospinning fiber (diameter=15 mm), freeze dried membrane (diameter=15 mm), and surface modified membrane (diameter=15 mm) were firstly sterilized using 75% ethanol and immersed in phosphate buffered saline (PBS) three times to replace the ethanol, then were placed in 24-well corning with an addition of silicon O-shaped ring (inner diameter=13 mm), thickness=1 mm) located above. LG-DMEM cell culture medium was used and cells were incubated at the density of $2 \times 10^4$ cell/well at the condition of 37° C. and 5% $CO_2$ for 24 hours and 72 hours. Cell morphology was observed using microscope, while the adhesion rate at 24 hours and the proliferation rate at 72 hours were calculated using DNA analog.

The cell calibration was plotted. The cell solution was set to 5 to 7 concentration gradients and 1 mL of each concentration was freeze dried for 12 hours and then dissolved in 1.5 mL of decomposition solution (55 mM sodium citrate, 150 mM sodium chloride, 5 mM cysteine HCL, 5 mM EDTA, 1 mg/21 mL papain) at 60° C. for 24 hours. After dissolving, 0.5 mL of the solution were taken and added to 5 mL of dye (10 mM Tris, 1 mM Na2DETA, 0.1 mM sodium chloride, 0.1 g/mL Hoechst). Fluorophotometer was used to detect the fluorescence intensity (Excitation wavelength=365 nm, Emission wavelength=458 nm). Standard curve of cell quantity was plotted by fluorescence intensity against cell concentration, and the amount of cells was calculated according to this standard curve.

Figure 12:
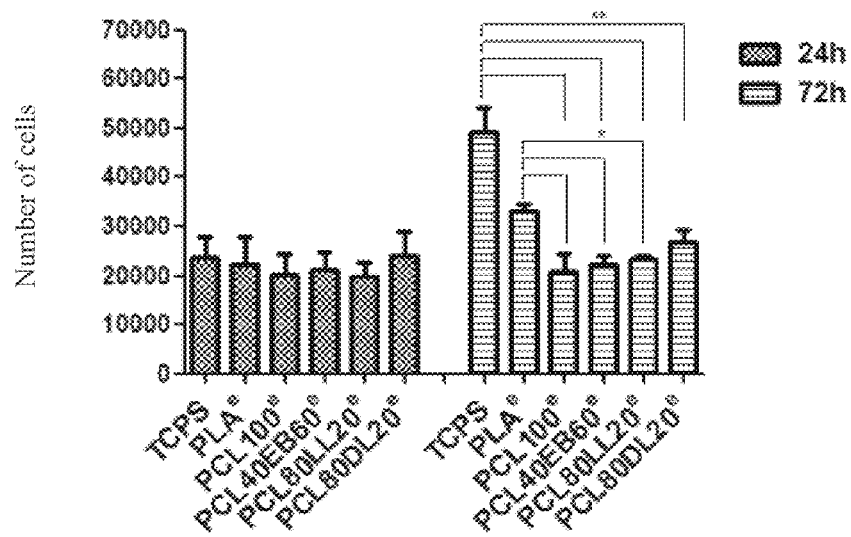
FIG. 12 is adhesion at 24 hours and proliferation 72 hours of endothelial cells (ECs) in the cell seeding density of $2\times10^4$ cell/well using different electrospinning fibers. (*$p<0.05$; **$p<0.05$)

FIG. 12 represents the results of cell adhesion and proliferation of endothelial cells using different electrospinning fibers. No significant difference regarding cell adhesion can be seen at 24 hours, however, after 72 hours, the growth and elongation of the endothelial cells along the waterborne biodegradable polyurethane electrospinning fiber can be observed. PCL80DL20$^e$ results in the highest proliferation rate.

Figure 13:
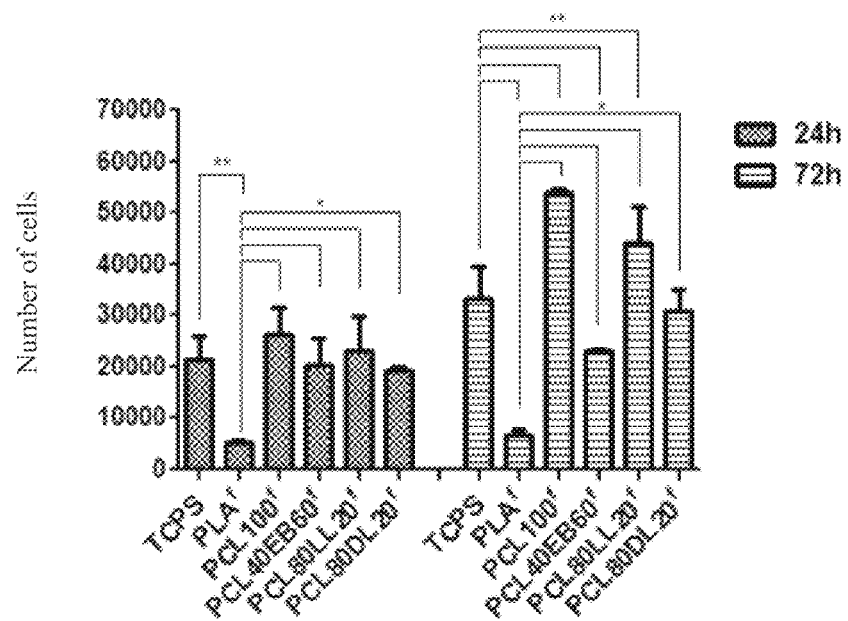
FIG. 13 is adhesion at 24 hours and proliferation 72 hours of endothelial cells (ECs) in the cell seeding density of $2\times10^4$ cell/well using different freeze dried membrane. (*$p<0.05$; **$p<0.05$)

FIG. 13 represents the results of cell adhesion and proliferation of endothelial cells using different freeze dried membrane. At 24 hours, the cell adhesion rate of the freeze dried waterborne biodegradable polyurethane membrane are all significantly higher than the cell adhesion rate of PLA$^f$, however, shows no significant difference comparing to TCPS. The cell proliferation rate of biodegradable polyurethane is still higher than the cell proliferation rate of PLA$^f$, PCL100f and PCL80LL20$^f$, in particular, are higher than TCPS.

Figure 14:
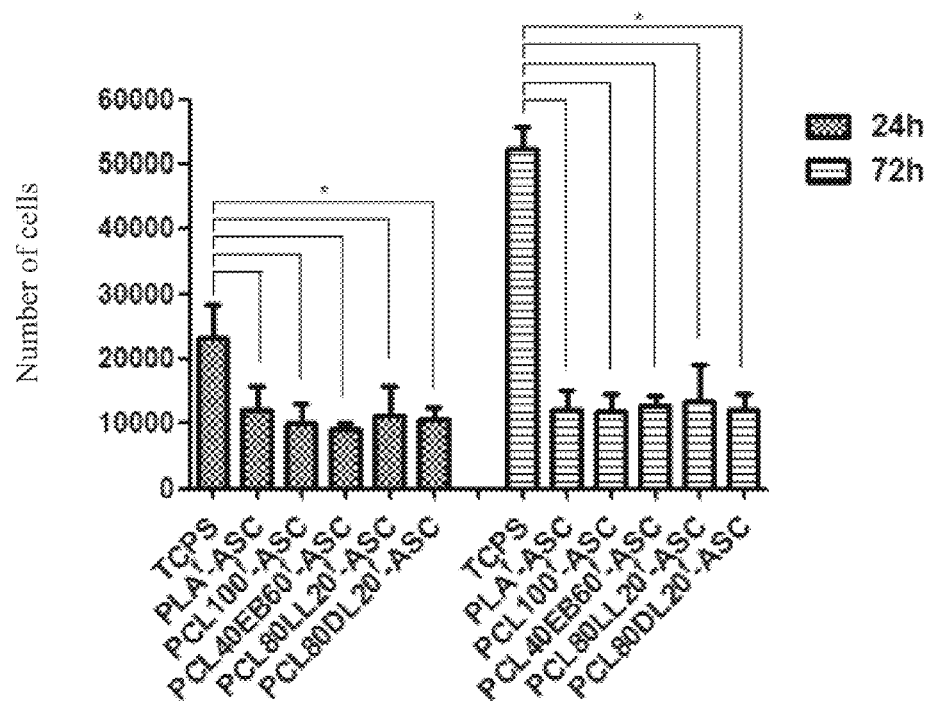
FIG. 14 is adhesion at 24 hours and proliferation 72 hours of endothelial cells (ECs) in the cell seeding density of $2\times10^4$ cell/well using freeze dried membrane with surface modification. (*$p<0.05$)

FIG. 14 represents the result of cell adhesion and proliferation of endothelial cells using different surface modified and freeze dried membrane. At both 24 hours and 72 hours, the cell adhesion rate and proliferation rates of the surface modified and freeze dried membrane show no significant difference comparing to PLA$^f$-ASC. The proliferation rate of PCL80LLD20$^f$-ASC is the highest.

4-2 Seeding Rate of Adipose-Derived Stem Cell

Rat adipose-derived adult stem cells from 3 to 5 generations were used. The freeze dried waterborne biodegradable polyurethane scaffold was sterilized using ultraviolet light for an hour and placed into 24-well corning. Low glucose DMEM/F12 (low glucose Dulbecco's modified Eagle's medium/nutrient mixture F-12, DEME-LG/F12=1:1, Gibco) cell culture medium containing 10% FBS, 1% PS, and 1.5 g/L $Na_2CO_3$ were used and the density of seeding cell concentrate was $150 \times 10^4$ cells/μL. With additions of 5 μL culture medium after 5 minutes, 100 μL, culture medium after 10 minutes, and 200 μL culture medium after 30 minutes followed by continuous addition of 200 μL culture medium each hour, the total volume was adjusted to 1 mL. Cells were then incubated for 24 hours under conditions of 37° C. and 5% $CO_2$.

The freeze dried scaffold after incubation with cells was freeze dried for 12 hours, then 1.5 mL of decomposition solution were added at 60° C. and the reaction was allowed to take place for 24 hours. 0.5 mL of the solution after decomposition were added to 5 mL of dye and the fluorescence intensity (Excitation wavelength=365 nm, Emission wavelength=458 nm) was measured using fluorphotometer. The amount of cells was calculated according to the standard curve, while the seeding rate was calculated according to Formula 3.

$$\text{Seeding rate (\%)}(NE-N) \times 100 \qquad \text{Formula 3}$$

Figure 15:
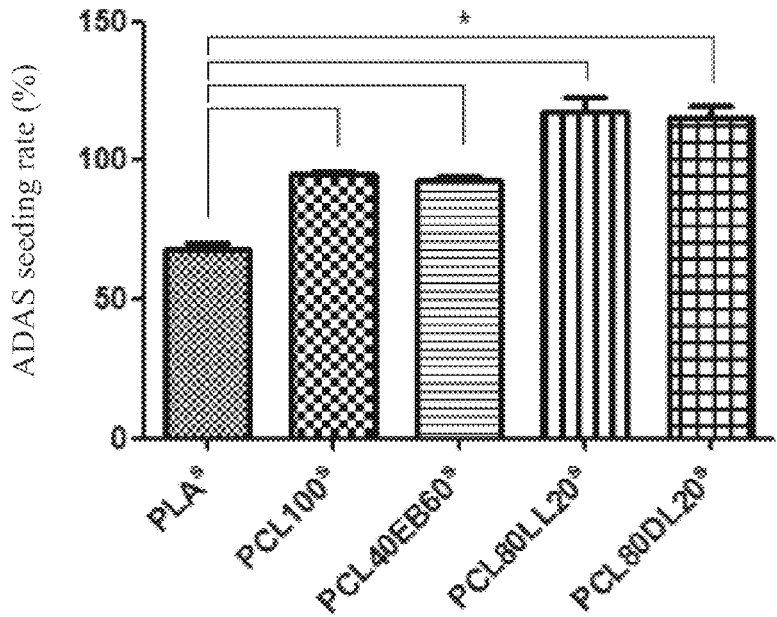
FIG. 15 is seeding rate of rat adipose-derived stem cells (rADAS) at 24 hours using different freeze dried scaffold. (*$p<0.05$)

NE is the number of cells after culturing for 24 hours, and N is $150 \times 10^4$ cells.

rADAS was used to test the seeding rate, and as shown in FIG. 15, the seeding rate of PCL100$^s$, PCL40EB60$^s$, PCL80LL20$^s$, and PCL80DL20$^s$ scaffold were all greater than 90%, whereas the minimum seeding rate of PLC scaffold is 63.9±8.4%. Besides, the seeding rate of PCL80LL20$^s$ and PCL80DL20$^s$ are 127.4±23.7% and 118.1±25.8%, respectively, indicating that cells can be successfully seeded onto scaffold, and can survive and proliferate without the requirement of wet condition.

4-3 Adhesion of Blood Platelet

The freeze dried waterborne biodegradable polyurethane membrane and surface modified membrane were cut into appropriate size and were attached to aluminum plate (diameter=2.4) using double adhesive tape. Then the plate was immersed in Hepe-Tyrodes buffer solution for an hour. After the buffer solution was discharged, blood platelet concentrate was added to fully cover the aluminum plate and allowed to settle in 5% $CO_2$ incubation camber for an hour. Blood platelets that did not adhere to the aluminum plate were washed away by washing with Hepe-Tyrodes buffer for three times, and then Hepes solution containing 2% (v/v) glutaraldehyde (Riedel-deHaen) were added. Blood platelets were fixed for 30 minutes and Hepes-Tyrode/double-distilled water solutions with concentration gradient were used to immerse the plate for 1 minute to eliminate the salt on the surface. Same concentration gradient was applied and replaced with ethanol, and the plate was freeze dried using freeze dryer (FDU-1200, Eyela, Japan). Finally, the activation condition of the blood platelet adhered onto the surface of the plate was observed using scanning electron microscope (SEM, S-4800, Hitachi).

Figure 16:
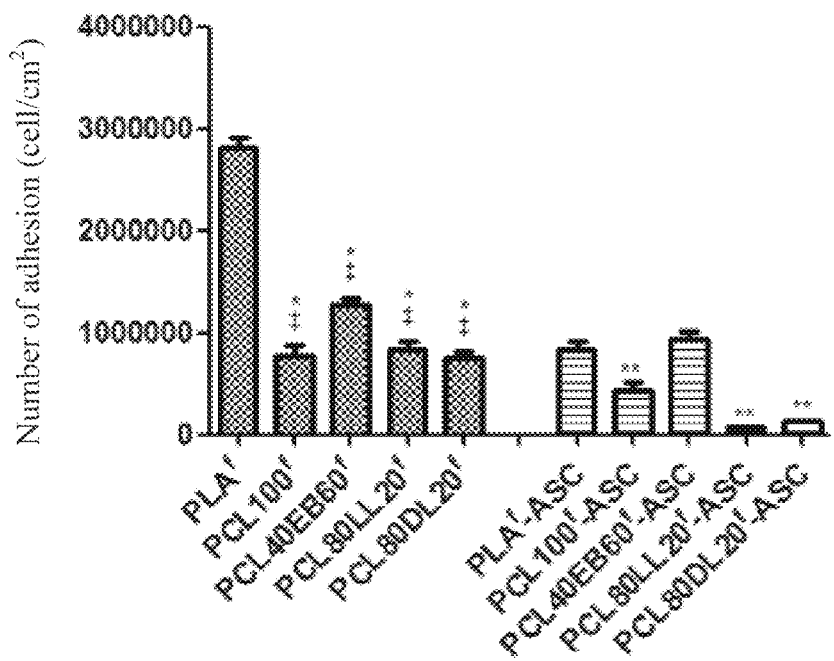
FIG. 16 is amount of blood platelet adhesion using different freeze dried membrane. (*$p<0.05$; **$p<0.05$; ‡$p<0.05$)

The amount of blood platelet adhered onto the surface and their activation degree before and after modifying the surface by sulfonated chitosan can be used as indications for blood compatibility. As shown in FIG. 16, considerable adhesion and activation of blood platelet can be observed before the surface modification, and $PLA^f$, in particular, is significantly higher than the others. A tendency to decrease regarding blood platelet adhesion and activation can be observed after the surface modification, wherein $PCL40EB60^f$-ASC is not significantly different from $PLA^f$-ASC; $PCL100^f$-ASC, $PCL80LL20^f$-ASC, and $PCL80DL20^f$-ASC are significantly lower than $PLA^f$-ASC. Particularly, $PCL80LL20^f$-ASC and $PCL80DL20^f$-ASC show negligible blood platelet adhesion and activation, indicating that the modification does not result in blood coagulation.

The amounts of blood platelet adhesion before surface modification are rated as follow: $PLA^f > PCL40EB60^f > PCL100^f > PCL80LL20^f \approx PCL80DL20^f$; the levels of blood platelet activation are rated as follow: $PCL40EB60^f > PLA^f > PCL100^f \approx PCL80LL20^f \approx PCL80DL20^f$.

The amounts of blood platelet adhesion after surface modification are rated as follow: $PLA^f$-ASC$\approx$PCL40EB60$^f$-ASC>PCL100$^f$-ASC>PCL80DL20$^f$-ASC$\approx$PCL80LL20$^f$-ASC.

The levels of blood platelet activation are rated as follow: $PLA^f$-ASC>PCL40EB60$^f$-ASC$\approx$PCL100$^f$-ASC>PCL80DL20$^f$-ASC$\approx$PCL80LL20$^f$-ASC.

Thus, according to the above embodiments, compositions of PCL40EB60, PCL80LL20, and PCL80DL20 are found to be capable of being made into waterborne biodegradable polyurethane emulsion in Example 1. Example 1 also further instructs the emulsion being made into biocompatible and biodegradable polyurethane in the form of membrane. Example 2 discloses that the inflammatory response caused by the membrane is not significant and proofs that, via in vitro and in vivo degradation test, the biocompatible and biodegradable polyurethane exhibit biocompatibility and biodegradability. According to Example 3, by using electrospinning, freeze drying, and particle-leaching/freeze drying, scaffolds with diameters of pores on the surface and the cross-section sit within the range of the diameter of vascular graft endothelialization can be prepared. Example 4 further proofs that the scaffold made in Example 3 does not posses significant blood coagulation function. Moreover, cells such as endothelial cells and adipose-derived stem cells can successfully implant onto the scaffold and proliferate, indicating biocompatibility, hence, being one ideal material for vascular graft.

Figure 17:
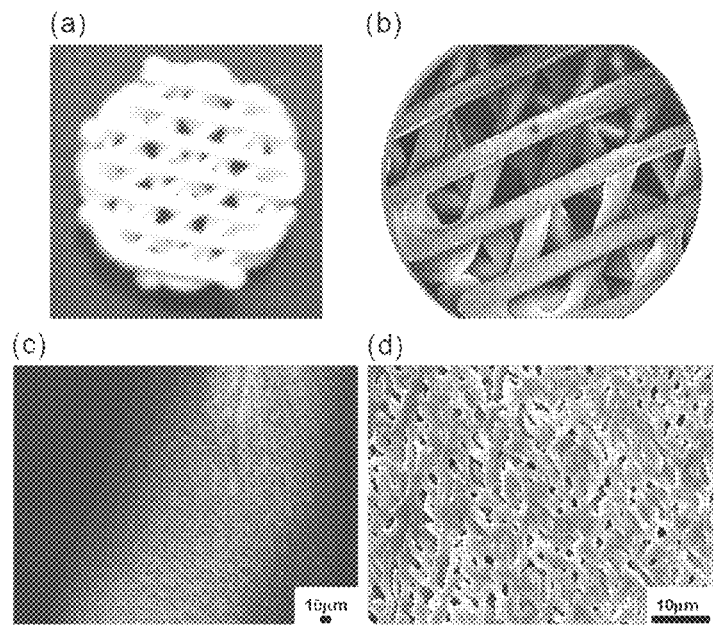
FIG. 17 is the structurally opened 3D scaffold with stacking regular micropillar made by waterborne biodegradable polyurethane emulsion, wherein (a) is the visible appearance and (b to d) are SEM images with different magnifying powers.

In addition, the waterborne biodegradable polyurethane was also prepared in the form of structurally opened 3D scaffold with stacking regular micropillar (as shown in FIG. 17). Micropores with diameter of 1.94±0.6 μm were also found to be spreading along each nanopillar. Pores of this size are beneficial for the maintenance of cell morphology, thus can be applied to sophisticated cell scaffold.

To understand whether the abovementioned scaffold is suitable for the incubation of mesenchymal stem cell, polyurethane sophisticated scallfold were sterilized for a day using ultraviolet light. Then, mesenchymal stem cells were used to carrier out the cell seeding experiment. Adipose-derived stem cells were extracted from rat adipose tissue, in which $1 \times 10^6$ cells were suspended in 20 mL of culture solution to form a cell concentrate. The cell concentrate was then seeded onto polyurethane scaffold and incubated for 4 hours. Finally, 3 mL of culture solution were added and the incubation was allowed to proceed for another 20 hours. DNA dye Hoechst 33258 was used to perform cell count. The results indicates that after 24 hours of incubation, the number of cells is between $8.59 \times 10^5$ to $8.77 \times 10^5$ and the seeding rate is 86.8±0.9%, showing that the scaffold is suitable for the incubation of mesenchymal stem cells such as adipose-derived stem cells.

Example 5

Microsphere Prepared by Using the Waterborne Biodegradable Polyurethane Emulsion Spraying process can be applied to the preparation of waterborne biodegradable polyurethane microsphere, for instance, directly spray the waterborne biodegradable polyurethane into liquefied nitrogen then undergo freeze drying. This process can also be incorporated by thermal-induced phase separation (TIPS) and wet-phase separation. The microsphere prepared has diameter of 20 to 60 μm with microporous structure.

Figure 18:
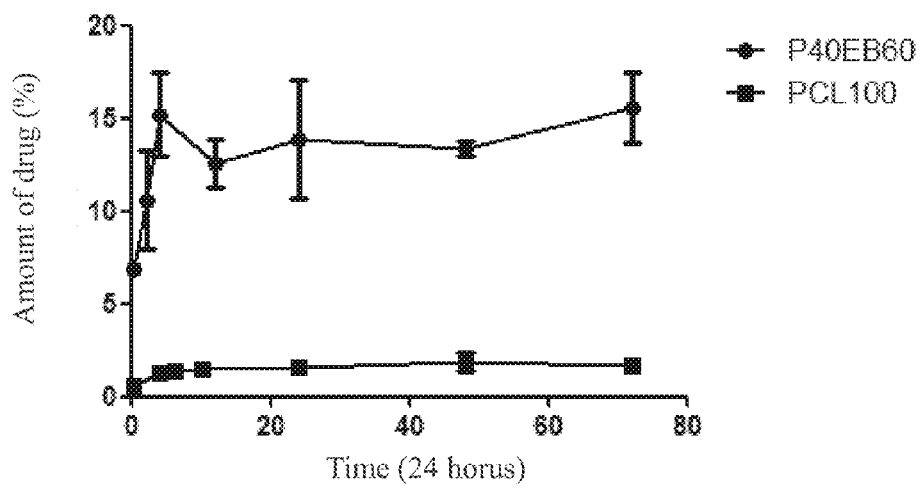
FIG. 18 is the drug carrying ability of PCL40EB60 microsphere and PCL100 microsphere.

To test the ability of microsphere as a drug carrier, firstly, methylene blue was mixed with waterborne biodegradable polyurethane PCL40EB60 and PCL 100. Then, microspheres having diameter of 20 μm were formed according to the above method. The microspheres having methylene blue were immersed in phosphate buffered saline (PBS) at 37° C. for 2, 4, 8, 12, 24, 48, and 72, hours, respectively. Then UV/vis spectrometer was used to measure the absorption at 660 nm for quantification. As shown in FIG. 18, the result of drug release of the microsphere, the amount of drug released of PCL40EB60 microsphere is much higher than the amount of drug released of PCL100 microsphere, however, both PCL40EB60 micosphere and PCL100 microsphere have drug carrying capabilities.

Figure 19:
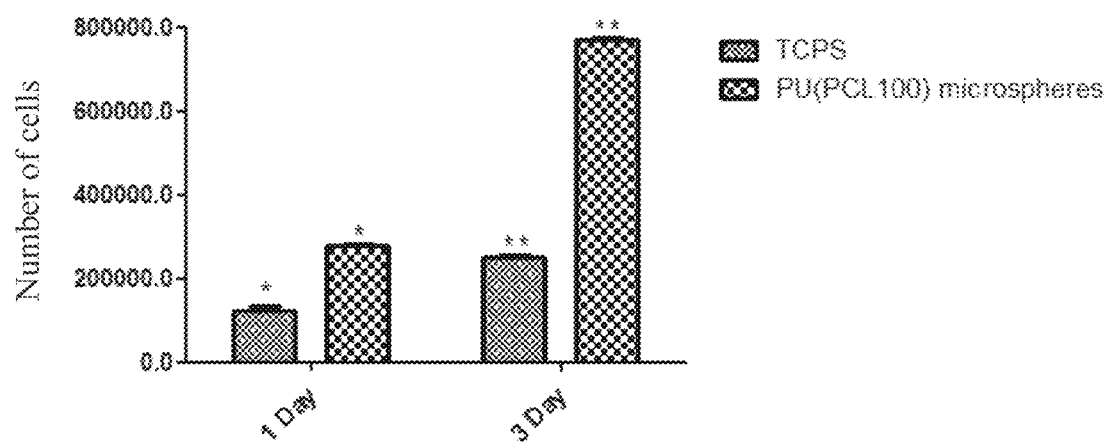
FIG. 19 is cell carrying ability of PCL100 microsphere.

In addition, the cell carrying capability of the microsphere was tested. L929 cell was loaded at a density of $1 \times 10^5$ cells/well. PCL100 microsphere was added (0.1 g/well) or TCPS was applied. The cells were then incubated under conditions of 37° C. and 5% $CO_2$ for 24 hours and 72 hours followed by observation of the number of cells. As shown in the result of FIG. 19, the number of cells incubated with PCL100 microsphere is significantly higher than the number of cells incubated by TCPS, indicating that PCL100 microsphere has cell carrying capability.

Example 6

Thermogelling Properties of Polyurethane

Synthesizing waterborne polyurethane emulsions as described in example 1, the soft segment of the polyurethane is 80 wt % polycarpolactone diol (PCL diol, Mw=2000 g/mol) and 20 wt % poly D,L-lactide diol (PDLLA diol, Mw=1500 g/mol), the polyurethane is represented by "PCL80DL20-1500" hereafter.

Figure 20:
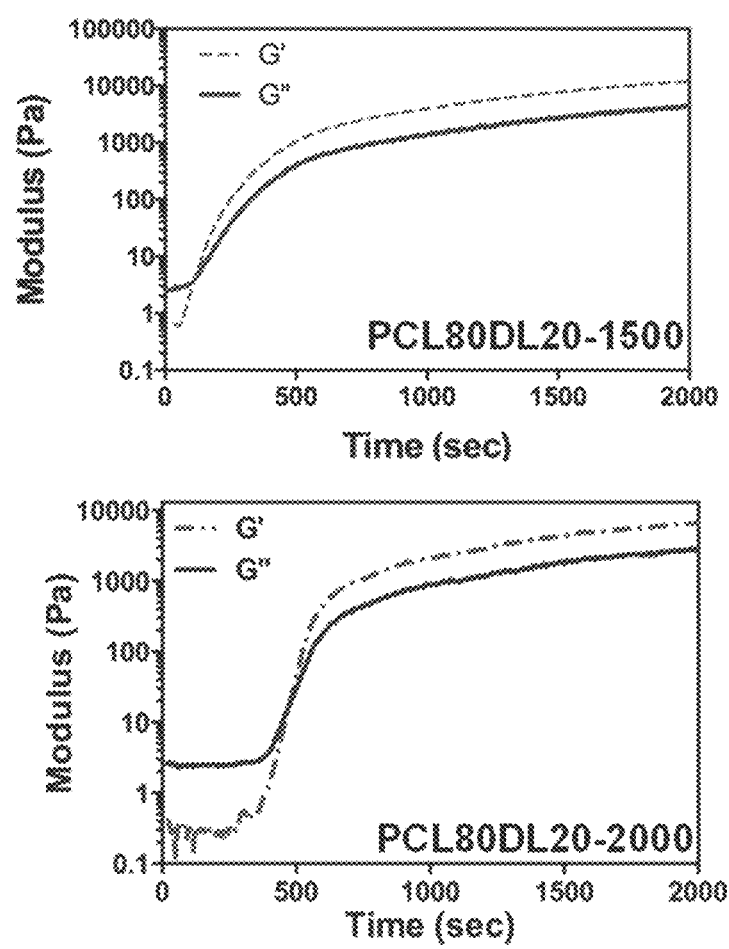
FIG. 20 shows rheograms of PCL80DL20-1500 and PCL80DL20-2000.

The PCL80DL20-1500 polyurethane emulsion can form hydrogel at temperatures higher than 37° C., this property is similar to the polyurethane emulsion PCL80DL20 (Mw of PDLLA diol is 2000 g/mol, represented by "PCL80DL20-2000" hereafter) disclosed in example 1. The rheological properties of PCL80DL20-1500 and PCL80DL20-2000 showed in Table 7 and FIG. 20.

TABLE 7

| | Molecular weight of PDLLA diol (Da) | Gelation Time (s) | Storage modulus (kPa) |
|---|---|---|---|
| PCL80DL20-1500 | 1500 | 100 | 12 |
| PCL80DL20-2000 | 2000 | 465 | 6.8 |

Figure 21:
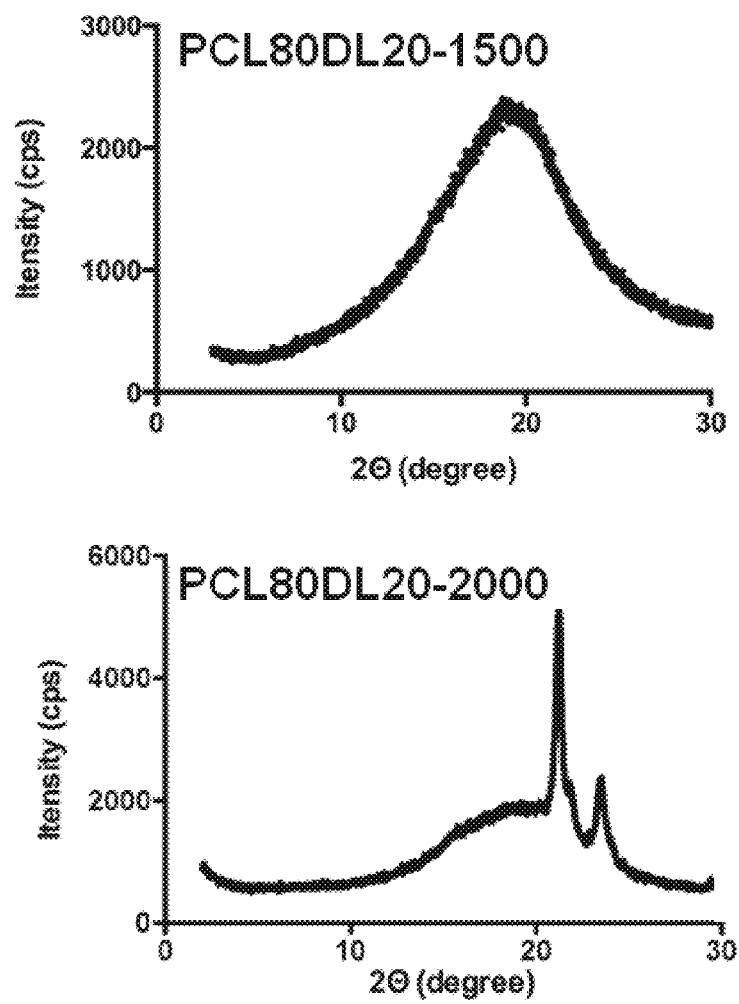
FIG. 21 shows WAXRD graphs of PCL80DL20-1500 and PCL80DL20-2000.

PCL80DL20-1500 polyurethane forms hydrogel faster than PCL80DL20-2000 polyurethane and its hydrogel strength is higher. On the other hand, PCL80DL20-2000 polyurethane crystalizes easier (FIG. 21), indicating that the intermolecular forces is stronger. In general, which has stronger intermolecular forces has faster hydrogel forming rate and higher strength. Our result is contrary to conventional concept.

According to the properties of PCL80DL20-1500 and PCL80DL20-2000, PCL80DL20-2000 is suitable for applying to softer tissue, for example, nerves, skin, muscle, blood vessels and cartilage; on the other hand, PCL80DL20-1500 is suitable for applying to harder tissue, for example, bone.

Example 7

Figure 22:
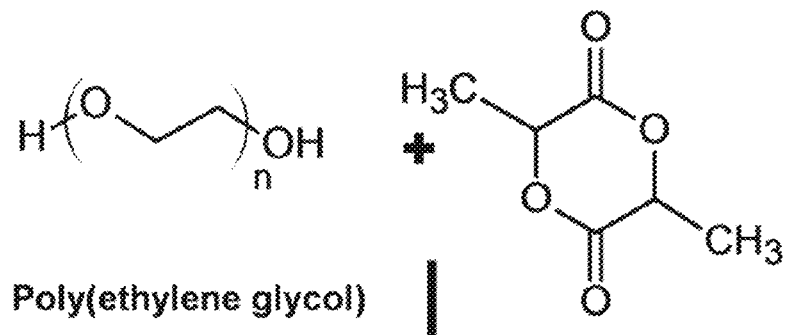
FIG. 22 shows the synthesis process for the diblock copolymers LE and DE and triblock copolymer LEL.
Figure 22:
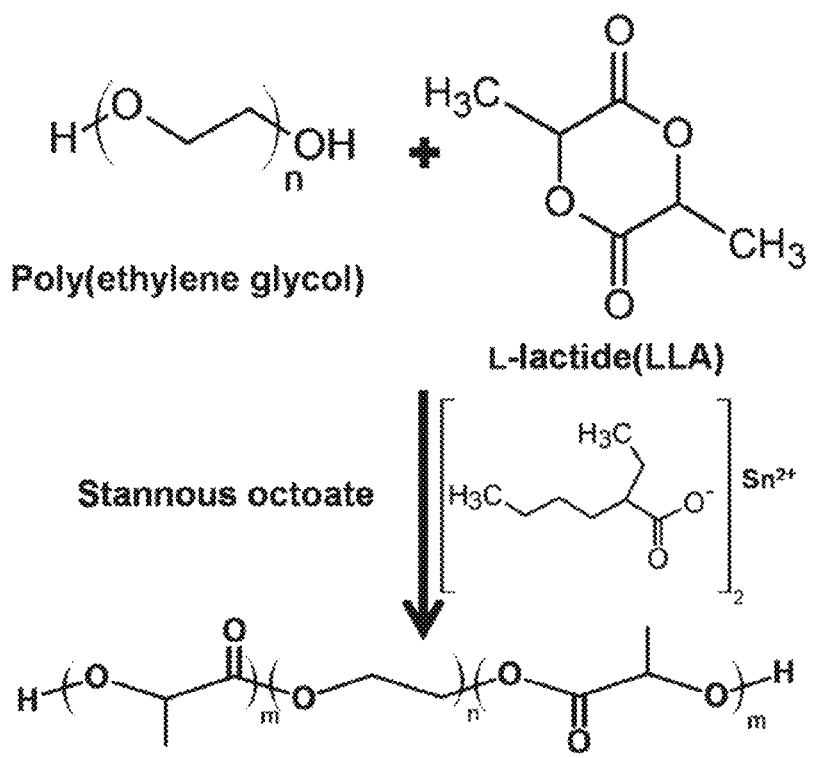

Thermogelling Properties of Polyurethane with Amphiphilic Blocks 7-1 Synthesis of Block Oligodiols Three types of block oligodiols were synthesized before the use in PU reaction, as shown in FIG. 22. They were poly(L-lactide-co-polyethylene glycol) ("LE") diol, poly(D-lactide-co-polyethylene glycol) ("DE") diol, and poly(L-lactide-co-polyethylene glycol-co-L-lactide) ("LEL") diol.

LE diol (Mn=3387) and DE diol (Mn=3297) were prepared as described below. L (or D)-lactide was obtained from Purac and monomethoxy poly(ethylene glycol) (mPEG, Mn=2000) was supplied by Fluka. L (or D)-lactide and mPEG were added into a flask. The molar ratio of ethylene oxide to lactate repeat units (ED/LA) was 45/19 for LE and 45/18 for DE. Zinc lactate (0.1 wt %) as the catalyst was then added. After degassing, the flask was sealed under vacuum and the polymerization was conducted at 140° C. After 7 days, the product was recovered by dissolution in dichloromethane ($CHCl_2$) and precipitation in diethyl ether. Finally, the product was dried under the vacuum.

LEL diol (Mn=2200) was prepared as described below. Poly(ethylene glycol) (PEG, Mn=1000) was supplied by Hanaka (Japan). Tin(II)2-ethylhexanoate (T-9) was from Alfa Aesar. PEG was dried in a vacuum oven at 150° C. for 3 days. L-lactide and PEG were placed in a 50 ml round-bottomed flask equipped with a stirrer. The reaction mixture was heated to 130° C. with stirring under $N_2$ and 0.05 wt % T-9 was then added. The mixture was stirred for 10 h at 130° C. The final product obtained was dissolved into $CHCl_2$ and cooled to 25° C. Subsequently, the products were extracted with a cold solvent mixture of methanol and n-hexane. Finally, the product was dried in a vacuum oven at 40° C. for 3 days.

7-2 Synthesis and Properties Measurement of Waterborne Polyurethane

Synthesizing waterborne polyurethane emulsions as described in example 1, the soft segment of the polyurethane is chosen from four kinds of oligodiols, which including poly (ε-caprolactone) (PCL) diol, LE diblock diol, DE diblock diol, and LEL triblock diol. The four kinds of oligodiols are synthesized in example 7-1. We synthesized eight polyurethane named PCL100, PCL90LE10, PCL90DE10, PCL80LEL20, PCL95LEL5, PCL95DED5, PCL70LL30 and PCL50LL50, the number behind the oligodiol abbreviation is the oligodiol's percentage of total soft segment.

The hydrodynamic diameter ($D_h$) of each type of PU NPs is listed in Table 8. PCL100 NPs had the largest $D_h$ of 39.3 nm Replacing a part of soft segment by amphiphilic blocks decreased $D_h$ values to 26-37 nm Particularly, PCL90LE10 NPs showed the smallest $D_h$ value. The zeta potential of various PU NPs was between −29 to −58 mV.

TABLE 8

The abbreviation of PU prepared in this study, the size and zeta potential of the nanoparticles, and the contact angle of the films

| | | | | | DLS | | |
|---|---|---|---|---|---|---|---|
| Abbreviation of PU | Molar percent of the PU soft segment (%) | | | | Hydrodynamic diameter | Zeta potential | Contact angle |
| | PCL | PLLA | PDLA | PEG | ($D_h$, nm) | (mV) | (°) |
| PCL100 | 100 | 0 | 0 | 0 | 39.30 ± 0.9 | −57.0 ± 2.1 | 83.04 ± 1.8 |
| PCL90LE10 | 90 | 2.969 | 0 | 7.031 | 26.85 ± 0.9 | −37.26 ± 1.8 | 23.51 ± 2.3 |
| PCL90DE10 | 90 | 0 | 2.857 | 7.143 | 37.07 ± 1.1 | −36.24 ± 2.7 | 55.83 ± 3.7 |
| PCL80LEL20 | 80 | 8.421 | 0 | 11.579 | 31.93 ± 0.5 | −29.3 ± 0.6 | 72.50 ± 1.4 |

On the other hand, PCL100 films showed the largest contact angle of 83.0°. Substituting the soft segment with a small fraction of amphiphilic blocks decreased the contact angle values to 23°-73°. Among the films, PCL90LE10 had the lowest contact angle of 23.5°. Therefore, PCL90LE10 films were the most hydrophilic among all samples.

Figure 23A:
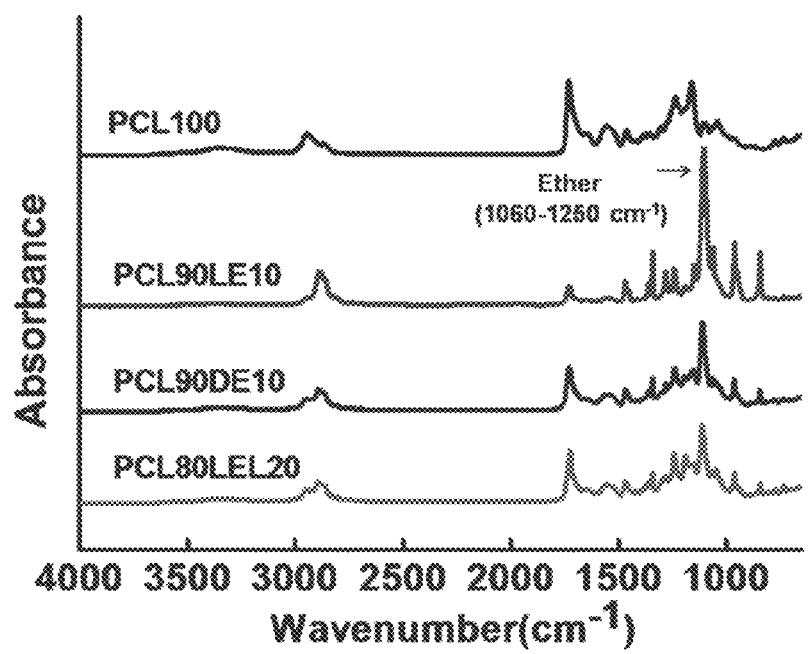
FIG. 23A shows ATR-IR spectra of the PU.
Figure 23B:
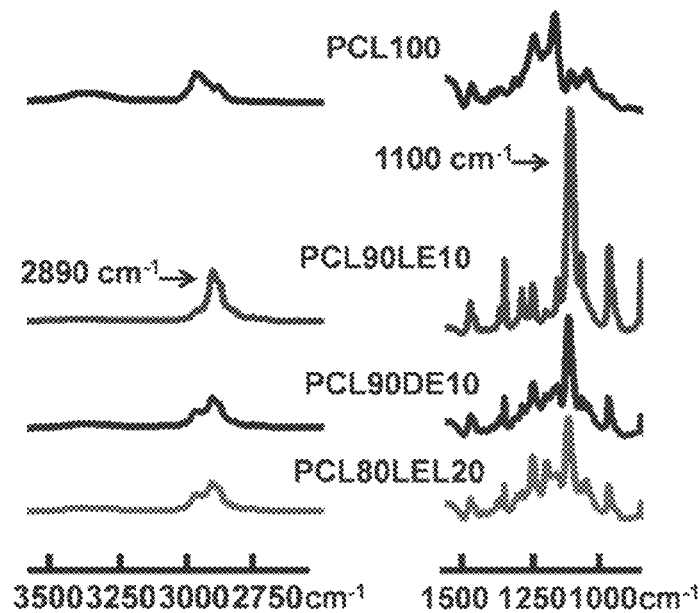
FIG. 23B shows enlarged ATR-IR spectra for the bands of C—H and C—O—C vibrations.

ATR-IR spectra of the PU films are shown in FIG. 23A. The stretching bands at 2260-2280 $cm^{-1}$ (—NCO group) and at 3200-3600 $cm^{-1}$ (O—H group) were absent in all sample films, confirming that the diisocyanate, oligodiols, and chain extenders had completely reacted during the PU synthesis. The absorption peaks at 3350 $cm^{-1}$ (N—H group) and 1730 $cm^{-1}$ (C=O group in urethane and ester) were observed for all PU films and were the strongest in PCL100 samples. The peak at 1060-1250 $cm^{-1}$ (C—O—C) was attributed to the symmetric and asymmetric stretching vibration of ester in all samples. The band in 2860-2900 cm$^{-1}$ (methylene) was attributed to the symmetric and asymmetric stretching of the methylene group. Enlarged ATR-IR spectra in the range of 2700-3600 cm$^{-1}$ and 1000-1500 cm$^{-1}$ are shown in FIG. 23B. For PU containing amphiphilic blocks, the absorption intensity at 1100 cm$^{-1}$ increased, which was associated with the stretching vibration of C—O—C (ether) in the EO block. The characteristic band at 2890 cm$^{-1}$ was originated from the stretching of CH$_2$ groups in EQ. PCL90LE10 revealed the highest absorption peaks at 1100 cm$^{-1}$ and 2890 cm$^{-1}$, indicating that PCL90LE10 surface was enriched with the EO block. The latter finding was consistent with the excellent surface hydrophilicity (low contact angle) observed for this sample.

Figure 24A:
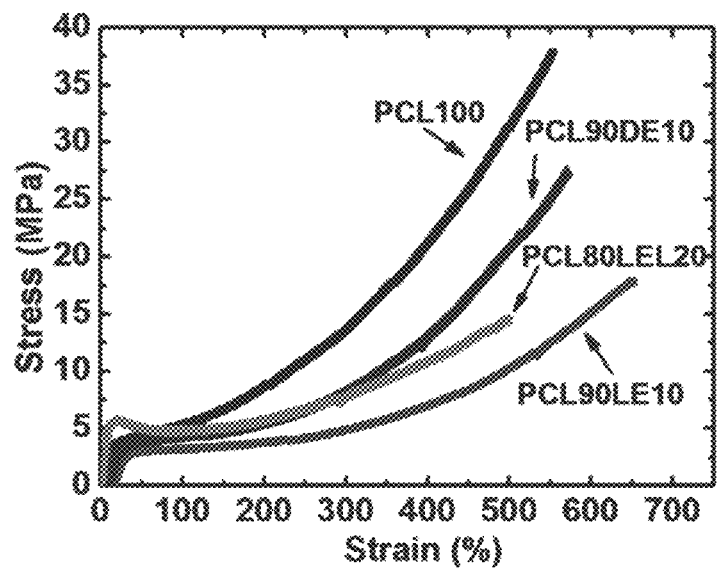
FIG. 24A shows typical stress-strain curves for various PU.

The tensile stress-strain curves of various PU films are shown in FIG. 24A. The Young's modulus, 100% modulus, tensile strength, and elongation obtained from the curves are summarized in Table 9. Among the films, PCL100 had the largest tensile strength (~35 MPa). PCL80LEL20 had the largest Young's modulus (~157 MPa) but the smallest tensile strength (~15 MPa) probably because of the higher LA contents of this polymer. The tensile strength of PCL90LE10 and PCL90DE10 (~19-25 MPa) fell between those of PCL100 and PCL80LEL20. All films showed the maximum elongation over 500%, indicating the elastomeric nature of all PU samples.

XRD profiles are displayed in FIGS. 25A-D. PCL100 revealed a broad band without any characteristic peak, i.e. it was amorphous in nature. On the other hand, PU introduced with amphiphilic blocks as soft segments showed characteristic peaks of crystallization. Peaks with the locations at 2θ=16.7° and 2θ=19.2° were associated with the LA and EO block, respectively. Peaks with the locations at 2θ=21.1° and 2θ=23.3° were associated with PCL. The degree of crystallinity for PU films is listed in Table 10. PCL90LE10 had the largest degree of crystallinity (~14%). Moreover, the crystalline EO block in PCL90DE10 and PCL90LE10 may account for their microphase separation in comparison with the less crystalline EO block in PCL80LEL20.

The prepared PU was stored in a refrigerator (10° C.) before investigation of the gelation behavior in room temperature over a period of time. Slow gelation at an average temperature of 26° C. was observed. PCL90LE10 was gel-like on the fifth day, while PCL90DE10 formed a viscous fluid (semi-gel-like) on the fifth day and was gel-like on the seventh day. PCL80LEL20 showed a similar tendency of gelation as PCL90DE10. The above gross observation revealed that the hydrophilicity (hydration) and degree of crystallinity might contribute to gelation. PCL90LE10 was subjected to further analyses because of its favorable gelation time and low percentage of amphiphilic blocks.

TABLE 9

The tensile properties (at 25° C.) and thermal properties of PU films

| | Young's modulus (MPa) | 100% modulus (MPa) | Tensile strength (MPa) | Elongation at break (%) | $T_{onset}$ (° C.) | $T_d$ (° C.) |
|---|---|---|---|---|---|---|
| PCL100 | 30.9 ± 7.9 | 5.30 ± 0.1 | 34.9 ± 3.1 | 535.5 ± 19 | 266.0 | 372.2 |
| PCL90LE10 | 18.6 ± 2.8 | 3.16 ± 0.3 | 18.8 ± 1.2 | 650.6 ± 10 | 236.4 | 343.5 |
| PCL90DE10 | 15.7 ± 1.5 | 4.13 ± 0.2 | 25.2 ± 1.5 | 573.3 ± 2.3 | 243.9 | 347.7 |
| PCL80LEL20 | 157.0 ± 22 | 4.77 ± 0.3 | 14.7 ± 3.7 | 500.0 ± 14 | 231.5 | 334.8 |

Figure 24B:
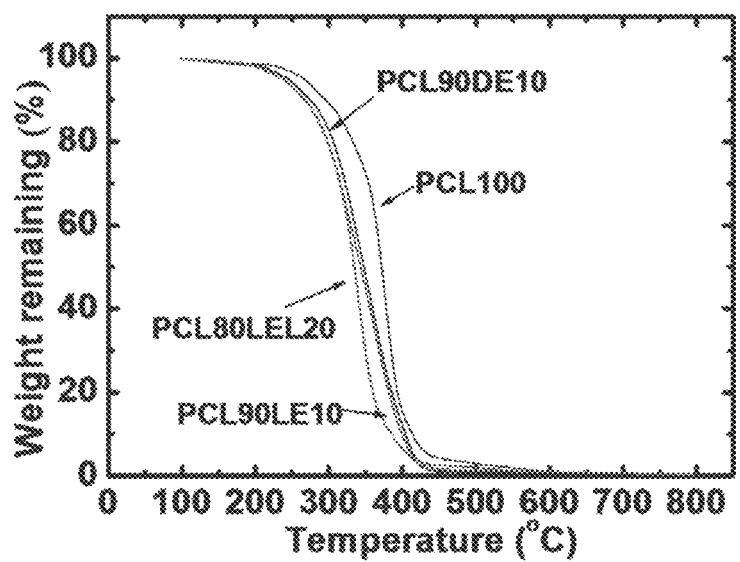
FIG. 24B shows TGA curves of PU.
Figure 25A:
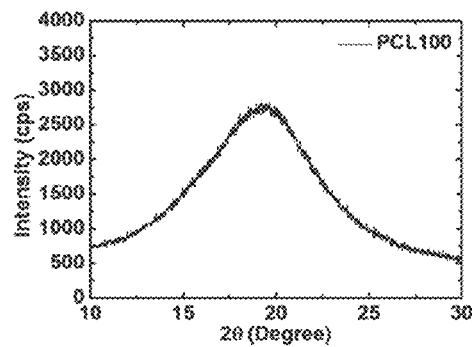
FIG. 25A shows typical X-ray diffraction patterns of PCL100.
Figure 25B:
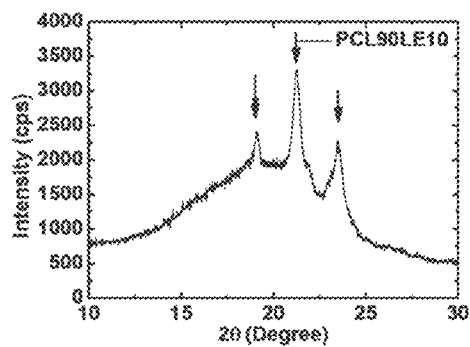
FIG. 25B shows typical X-ray diffraction patterns of PCL90LE10.
Figure 25C:
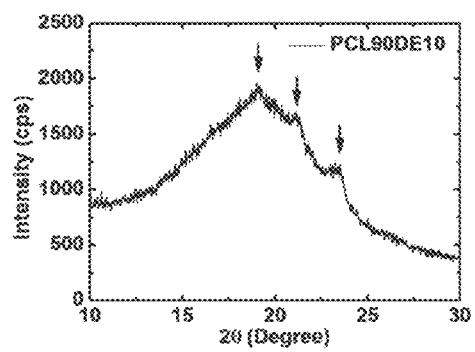
FIG. 25C shows typical X-ray diffraction patterns of PCL90DE10.
Figure 25D:
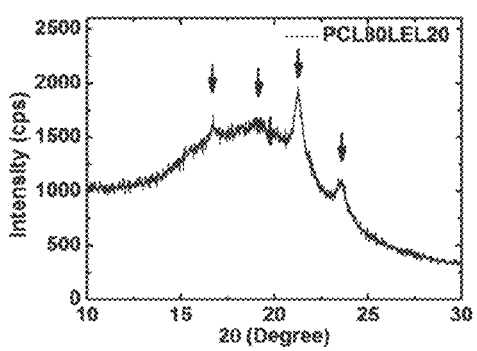
FIG. 25D shows typical X-ray diffraction patterns of PCL80LEL20.

TGA curves of PU are shown in FIG. 24B. The onset decomposition temperature ($T_{onset}$) and thermal decomposition temperature ($T_d$) are listed in Table 9. PCL100 had the highest $T_{onset}$ and $T_d$ while PCL80LEL20 had the lowest $T_{onset}$ and $T_d$. The thermal stability of the materials are ranked in the order of PCL100>PCL90DE10>PCL90LE10>PCL80LEL20. The glass transition temperature ($T_g$) of PU is shown in Table 10. PCL100 had the smallest $T_g$ while PCL80LEL20 had the highest $T_g$. Based on the above analyses, the degree of microphase separation was the greatest in PCL100, followed by PCL90DE10 and PCL90LE10, and was the smallest in PCL80LEL20.

Figure 26A:
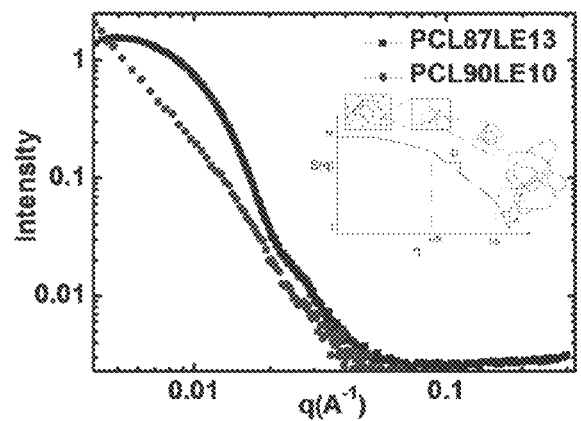
FIGS. 26A-C shows SAXS profiles of PCL87LE13 and PCL90LE10 PU NP dispersion.
Figure 26B:
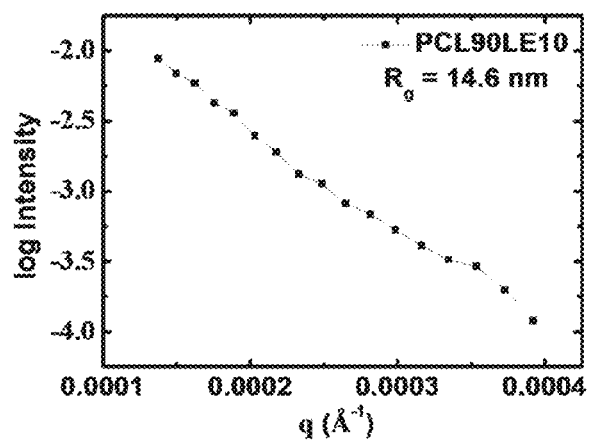
Figure 26C:
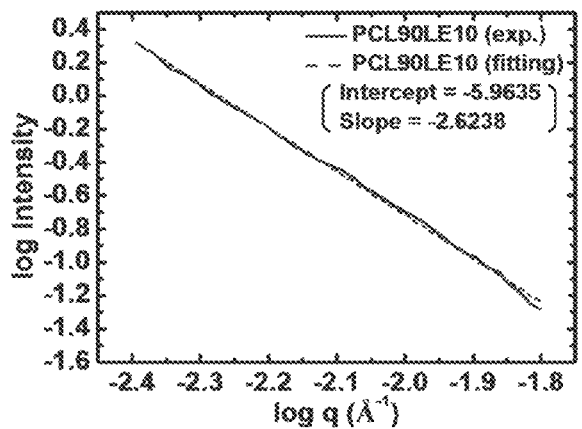

The SAXS profile of PCL90LE10 is shown in FIGS. 26A-C. The curve measured in 24 h after synthesis (FIG. 26A) revealed a relatively plateau region for scattering intensity at the low q region (0.001-0.01 Å$^{-1}$). For samples measured after gelling, the intensity dropped rapidly and the slope was steep even at low q region (FIG. 26B). Since the aggregation behavior of PCL90LE10 was time-dependent, two analytical methods were applied to account for the time-dependency. For non-aggregated PCL90LE10, the radius of gyration ($R_g$)) was estimated based on the Guinier analysis under the circumstance $qR_g<1.3$. The results of Guinier analysis showed an $R_g$ of 14.6 nm Additionally, as the ratio of LE got higher (PCL87LE13), the value of $R_g$

TABLE 10

DSC measurement of $T_g$ and $T_m$ and XRD calculation of the degree of crystallinity in PU films

| | DSC | | XRD peaks | | | |
|---|---|---|---|---|---|---|
| | $T_g$ (° C.) | $T_m$ (° C.) | PLA (2θ = 16.7°) | PEG (2θ = 19.2°) | PCL (2θ = 21.3°) | PCL (2θ = 23.5°) |
| PCL 100 | −53.06 | NA | NA | NA | 0 | 0 |
| PCL90LE10 | −51.57 | 60.78 | 0 | 0.99% | 8.35% | 4.69% |
| PCL90DE10 | −51.59 | 55.59 | 0 | 0.55% | 0.89% | 1.62% |
| PCL80LEL20 | −47.74 | NA | 0.42% | 0.24% | 3.75% | 1.28% |

$X_c$ = degree of crystallinity

Figure 27A:
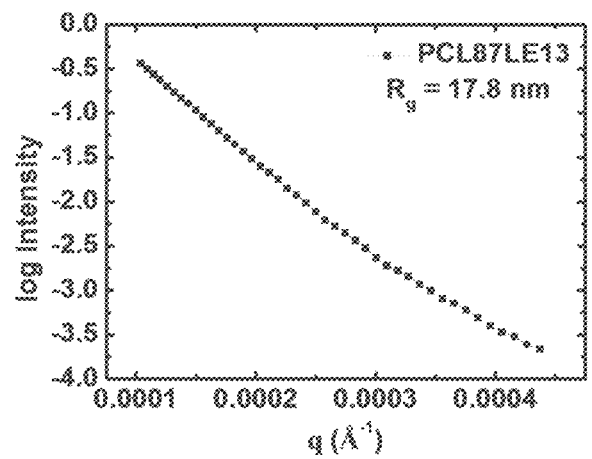
FIGS. 27A-B show SAXS profiles for the NP dispersion of PCL87LE13.
Figure 27B:
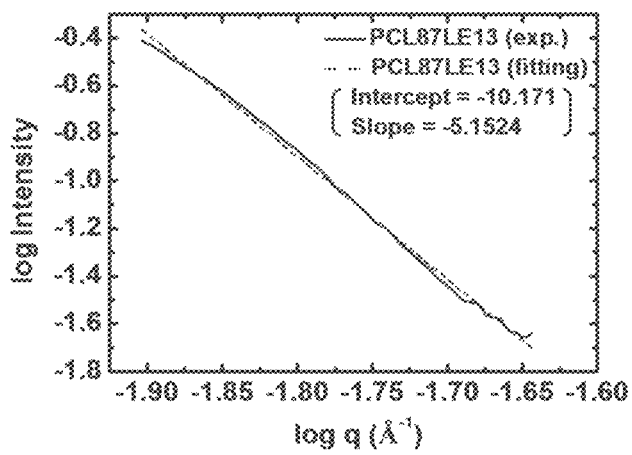

NA = Not applicable increased to 17.8 nm (FIGS. 27A-B). The ratio of $R_g/R_h$ (=$D_h/2$) of PCL90LE10 is 1.08. This ratio, which depends on the particle shape, is in the range of 0.9~1.1 for worm-like particles. For aggregated PCL90LE10, fractal analysis was used on q values ranging from 0.00404 to 0.01577 where a slope of −2.62 was obtained, as shown in FIG. 26C.

Figure 28A:
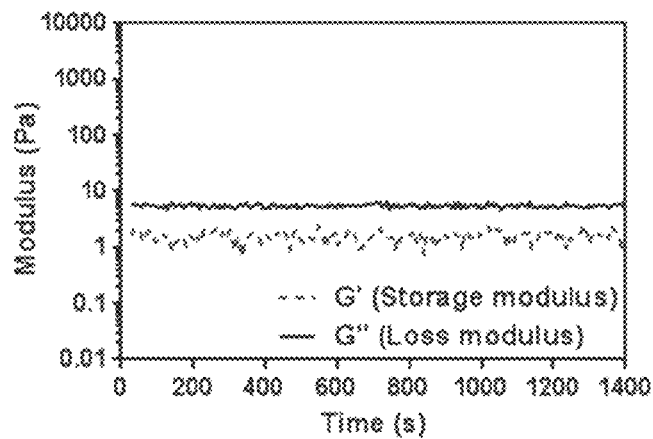
FIGS. 28A-C show time-dependent changes of storage modulus (G') and loss modulus (G") of PCL90LE10 upon exposure to various temperatures.
Figure 28B:
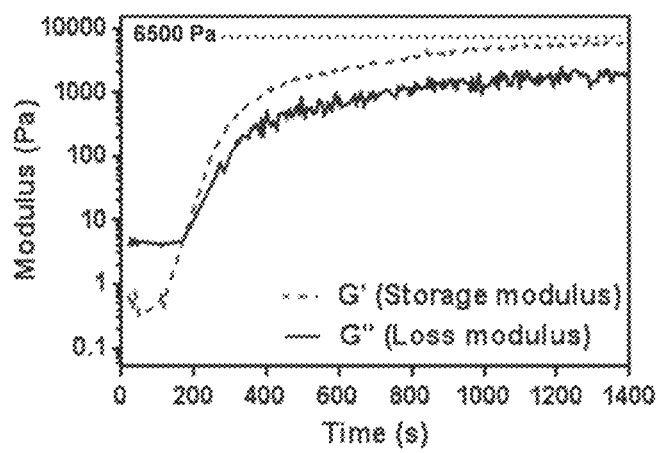
Figure 28C:
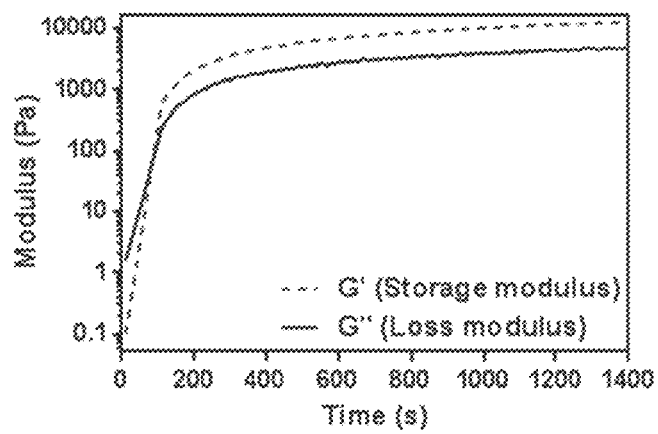
Figure 29A:
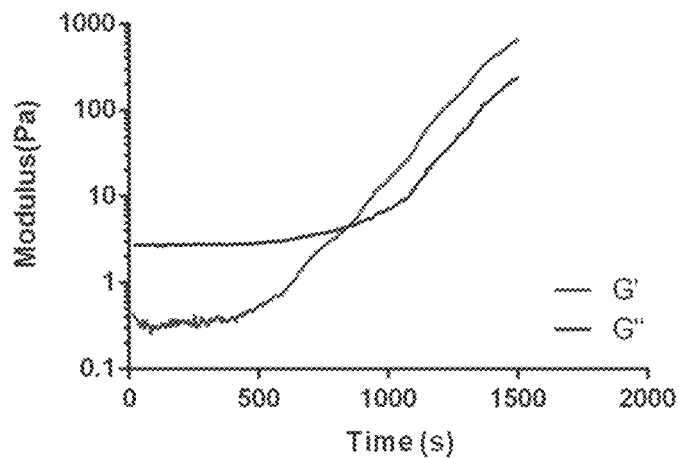
FIG. 29A shows time-dependent changes of storage modulus (G') and loss modulus (G") of PCL95LEL50.
Figure 29B:
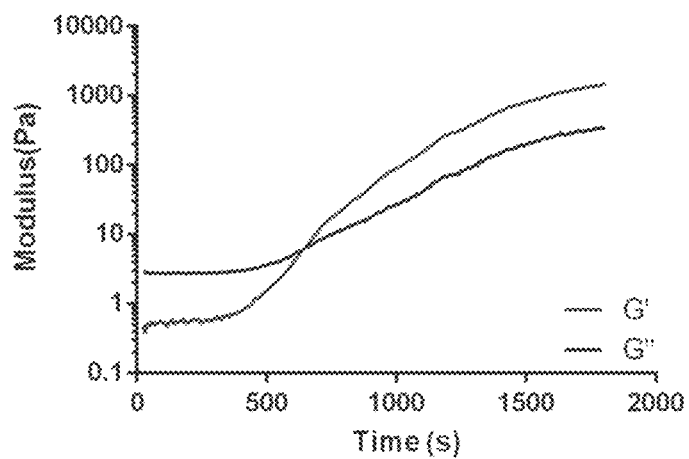
FIG. 29B shows time-dependent changes of storage modulus (G') and loss modulus (G") of PCL95DED5.
Figure 29C:
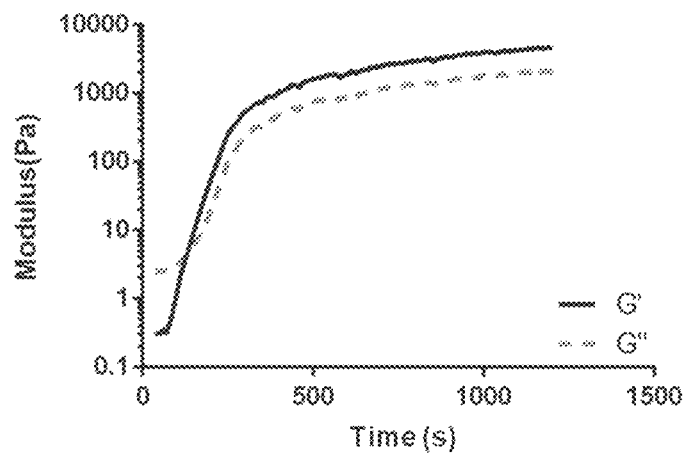
FIG. 29C shows time-dependent changes of storage modulus (G') and loss modulus (G") of PCL70LL30.
Figure 29D:
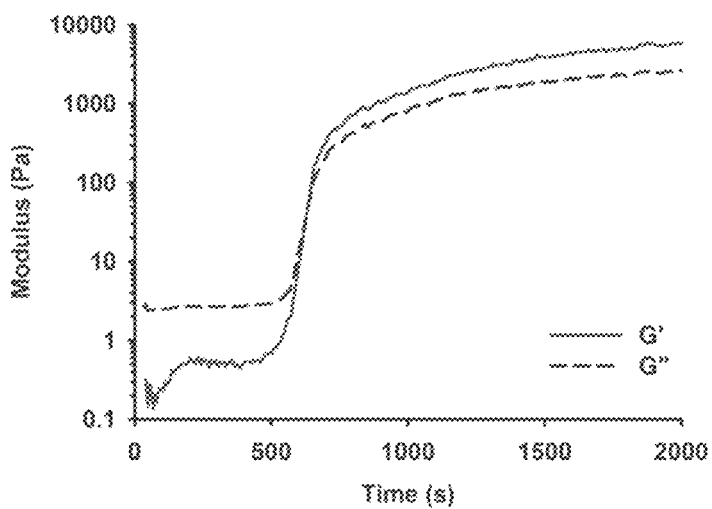
FIG. 29D shows time-dependent changes of storage modulus (G') and loss modulus (G") of PCL50LL50.

The rheological properties of PCL90LE10 at different temperatures are shown in FIGS. 28A-C. The approximate equilibrium gel modulus is listed in Table 11. When PCL90LE10 was placed under 25° C., the moduli G' and G" did not change significantly with time. When the temperature was maintained at 37° C., G' and G" crossed over after 169 s. The elastic modulus (G') reached ~6500 Pa in 20 min. When the temperature was controlled at 50° C., PCL90LE10 gelled after 84 s and G' reached ~12000 Pa in 20 min. These results indicated that PCL90LE10 gelled rather slowly below 25° C. but the gelation was obviously accelerated at higher temperatures.

TABLE 11

Gelation time of PCL90LE10 NP dispersion (solid content 30%) and approximate G' of the cured gel at various temperatures. The observation time was about 25 min.

| | PCL90LE10 | |
| --- | --- | --- |
| | Gelation time (s) | G' (Pa) |
| 25° C. (stable) | NA | NA |
| 37° C. | 169 | 6590 |
| 50° C. | 84 | 12242 |

PCL90LE10 with a solid content 30% was taken from the refrigerator and placed at 37° C. for 10 min and then loaded in a needle (26G, 260 μm). Gel formed after injection through the needle. When kept at 37° C., the gel could be deposited layer by layer. The gel was further printed at 37° C. using the 3D printer (FDM system). PCL90LE10 could be successfully printed.

To obtain whether cells can be embedded in the PU and printed with the gel, we done the following experiment.

Human umbilical cord derived mesenchymal stem cells (MSCs) were supplied by BIONET Corp (Taipei, Taiwan). MSCs were cultured in T150 tissue culture flasks (Falcon, BD Biosciences). The medium consisted of 10% fetal bovine serum (FBS; SAFC Biosciences, USA), 1.7 g/l sodium bicarbonate, and 1% antibiotic (Invitrogen). Cells were incubated in a humidified incubator with 5% $CO_2$ at 37° C. Cells of the eighth passages were used in this study. Before the 3D printing, cells were stained with a red fluorescent dye PKH26 (Sigma).

PCL90LE10 (30 wt %) was heated at 37° C. for 30 minutes. To perform the pre-test, the near-gelling emulsion was injected via a needle manually to prepare the fibers. The needle had a size of 26G (260 μm) and the emulsion was injected at a volumetric flow rate of 5.56 μl per second. Five to seven parallel arrays of fibers were injected to compose the first layer. The second layer was deposited at an angle of 90 degrees relative to the first layer. The constructs were placed in an incubator under 37° C. The above procedure may be repeated for 40 times to produce stacking layers.

PCL90LE10 (30%) was then mixed with cells (human MSCs) so that 1 ml of PCL90LE10 contained ~$2\times10^6$ cells. The near-gelling emulsion of PCL90LE10 was tested as the 3D printing ink by a fused deposition manufacturing (FDM) platform. Hydrogel scaffolds were prepared in 3 cm×3 cm square with 2 mm thickness. The syringe diameter was 260 μm. The stacking pattern of fibers was 0°/90°. The gas pressure was 35-40 psi and the volume flowrate was 1.67 μl per second. To print cell-containing hydrogel, PCL90LE10 (25-30 wt %) dispersion (2 ml) was mixed human MSCs at 25° C. and heated at 37° C. for 10 min before loaded to the needle of the 3D printer. After printing, cells were added 3 ml medium and incubated in a humidified incubator with 5% $CO_2$ at 37° C. Cell morphology was observed by fluorescence microscope after 0, 1, 2, 3, and 7 days.

PCL90LE10 (30%) was mixed with cells (human MSCs, ~$2\times10^6$ cells/ml) at 25° C. and heated at 37° C. for 10 min before loaded to the needle of the 3D printer. Cells can be embedded in the PU and printed with the gel, and the cells remained alive during a period of 7 days and could proliferate after 48 h. Gel with a lower solid content (25%) was also printed. Cells proliferated better in the more dilute gel. These results supported that PCL90LE10 sol-gel can be applied as a possible cell printing ink because of the thermoresponsiveness near 37° C.

The waterborne PU NPs prepared in this study had small hydrodynamic sizes and low zeta potentials, suggesting that all formulae may be stably dispersed in water. The negative charge was attributed to the $COO^-$ functional group in the hard segment. When the diblock or triblock copolymer diol replaced a small part of PCL diol, the NP size became smaller and the zeta potential increased (less negative). Besides, the surface contact angle of the cast films decreased. These changes may be associated with the introduction of more hydrophilic LA and EO blocks in the chemical structure of the PU. EO may form hydrogen bonding with water. When the PU contacts with water, the hydrophobic —$CH_2$—$CH_2$ turn inside and the hydrophilic C—O—C orient outside, increasing the hydrophilicity of the NP and cast films. The structure of PCL90LE10 may especially favor the orientation of C—O—C to the surface, causing the low contact angle of the film. This surface orientation of C—O—C was confirmed by ATR-IR. The ATR-IR spectra of PU did not show any peak around 2260-2280 $cm^{-1}$ (NCO) or 3200-3600 $cm^{-1}$ (OH), indicating that the synthetic reaction was complete. On the other hand, an evident peak was observed near 1060-1250 $cm^{-1}$ (asymmetric stretching C—O—C) for PU containing amphiphilic blocks. In particular, PCL90LE10 showed significant absorption near 1060-1250 $cm^{-1}$. These data, together with the low contact angle of PCL90LE10 films, suggested that PCL90LE10 surface had the most exposed EO blocks.

PCL100 had the best mechanical and thermal properties. This was because of the more abundant ester group in PCL100. Polyester type PU may form hydrogen bonding more readily than polyether type PU, contributing to greater tensile properties. Introducing LA/EO-containing block copolymer increased $T_g$. This is ascribed to the crystallization of soft segment. It was interesting to note that PCL80LEL20 had the largest Young's modulus and the smallest elongation. The low elongation was associated with the higher content of LA. The presence of LA probably contributed to crystallinity and low ductility.

PU based on 100% PCL diol (PCL100) demonstrated no crystalline peak in XRD. A previous study showed that introduction of 20% PLLA diol (PCL80LL20) may cause steric hindrance and secondary force, leading to crystallization of PCL as well as PLLA soft segments. This led to gelation at 37° C. with gel modulus (G') of 3500 Pa. The current study further introduced amphiphilic blocks containing PEO. The presence of PEO in limited amount may increase hydrogen bonding which promoted the self-assembly and raised the gel modulus to 6500 Pa. The hydrophilicity of PEO segregated the PCL soft segment and further increased its crystallinity. The crystallinity of PCL segment and its low $T_g$ allowed gelation to occur near body temperature. On the other hand, excessive PEO may prevent PCL from crystallization, as the case of PCL80LEL20. Although PEO segment may prolong the gelation time by preventing coagulation, the chain mobility in PU NPs increases as the temperature increases, which explains the fast gelation near body temperature. In addition, the PEO segment moves toward surface after water removal, the very hydrophilic surface of PCL90LE10 films (contact angle ~24°) may serve as non-fouling surface for other medical applications.

The fractal dimension of the PCL90LE10 gel at 37° C. was 2.6, as determined by the SAXS. This value was close to that predicted for a percolation cluster (~2.5). A common biopolymer, gelatin, was reported to have a $d_f$~2.5. Gelation has been employed as cell printing materials. For this purpose, gelation which is soluble in 37° C. should be cured by adding toxic photocrosslinkers, such as methacylate. Most body-temperature curable gels involve the block copolymers of PEO and propylene oxide (PPO) or those of PEO and PLA. The former family was non-biodegradable. The latter family may have acidic degradation products and the gel may be too weak (~1000 Pa) to be printed. The advantage of PCL90LE10 as a printing ink is its low viscosity at room temperature and rapid irreversible gelation near body temperature. This process is somewhat similar to gelation of collagen as reconstituted fibers. When the PU NP dispersion was mixed with cells at the solid contents of 30% or 25%, cells kept proliferating after printing. This confirmed the good cytocompatibility of the PU NP dispersion and gel. If the PU NPs was further diluted to 20%, gelation occurred very slowly and the gel collapsed after stacking. To be a proper candidate for 3D cell printing ink, the ink must have good cytocompatibility as well as physico-chemical and mechanical properties. The ink must solidify in order to stack layer by layer. Moreover, the ink must prevent cells from shear damage during printing. The structure of the gel should keep integrated after printing. The biodegradable PU NP dispersion/gel developed in this embodiment has low viscosity at 25° C. to facilitate mixing with cells, and quick gelation near body temperature. These features can make the PU NP dispersion/gel a novel material for 3D cell printing.

PU with soft segment containing 10-20% amphiphilic blocks demonstrated significantly different properties from PU with 100% PCL diol as the soft segment. Among them, PCL90LE10 had the lowest surface contact angle about 24° and the highest degree of crystallinity near 14%. ATR-IR spectra showed that the surface was enriched with EO blocks, which may increase the extent of microphase separation. The dispersion had low viscosity below room temperature. When the temperature was raised to close to body temperature, the dispersion reached the gel point after ~170 s and had good gel modulus ~6.5 kPa in 20 min. The dispersion of proper solid content (25-30%) could be printed together with stem cells at 37° C. Cells were proliferated in the deposited layers. The PU hydrogel is a smart thermo-responsive gel near body temperature, and a novel 3D printing ink for cell/tissue printing.

As show in Table 12 to Table 15 and FIG. 29A to FIG. 29D, the present invention synthesizes PCL95LEL5, PCL95DED5, PCL70LL30 and PCL50LL50. Gelation time is the time required for sol to gel phase transition and is defined by rheology as the point where storage modulus (G') and loss modulus (G") intersects with each other. The storage modulus also been defined as gel strength. The storage modulus of PCL95LEL5, PCL95DED5, PCL70LL30 and PCL50LL50 at 37° C. for 20 min is 173 Pa, 387 Pa, 4722 Pa, and 2444 Pa respectively.

TABLE 12

Gelation time of PCL95LEL5 (PCL diol:LEL diol = 95:5)

| Molecular weight (g/mol) | | | Gelation time |
|---|---|---|---|
| | LEL diol | | |
| PCL diol | PLLA | PEG | (sec) |
| 2000 | 1800 | 8000 | 840 |

TABLE 13

Gelation time of PCL95DED5 (PCL diol:DED diol = 95:5)

| Molecular weight (g/mol) | | | Gelation time |
|---|---|---|---|
| | DED diol | | |
| PCL diol | PDLA | PEG | (sec) |
| 2000 | 1728 | 8000 | 698 |

TABLE 14

Gelation time of PCL70LL30 (PCL diol:PLLA diol = 70:30)

| Molecular weight (g/mol) | | Gelation time |
|---|---|---|
| PCL diol | PLLA diol | (sec) |
| 2000 | 2100 | 176 |

Gelation time of PCL50LL50 (PCL diol:PLLA diol = 50:50)

| Molecular weight (g/mol) | | Gelation time |
|---|---|---|
| PCL diol | PLLA diol | (sec) |
| 2000 | 1300 | 656 |

Example 8

Cell and Plasmid Embedded in the PU and Transfection

PCL80DL20-1500 and PCL80DL20-2000 was heated in 37° C. incubator. Preparing 25 wt % PCL80DL20-1500 or PCL80DL20-2000 contains $2.5 \times 10^6$ cells/ml hMSCs (Human umbilical cord derived MSCs; BIONET Corp., Taiwan), 50 µg/ml GATA4, MEF2C or TBX5 plasmid (and a control group without plasmid) and serum-free medium. The hydrogels were injected via a needle with a 27 G needle head (inner radius of 200 µm). The hydrogels were injected with 55 kPa in a 3 cm Petri dish with 90° cross stacked. When the printing accomplished, adding serum-free medium and incubate for 1 day, then change the medium to serum containing medium and incubate for 2 days (3 days after printing). The control group was $2.5 \times 10^6$ cells/ml hMSCs with or without 50 µg/ml plasmid (GATA4, MEF2C and TBX5) in tissue culture polystyrene (TCPS), adding serum-free medium and incubate for 1 day, then change the medium to serum containing medium and incubate for 2 days. All groups were collected for analyzing cardiac-associated gene expression level.

Figure 30:
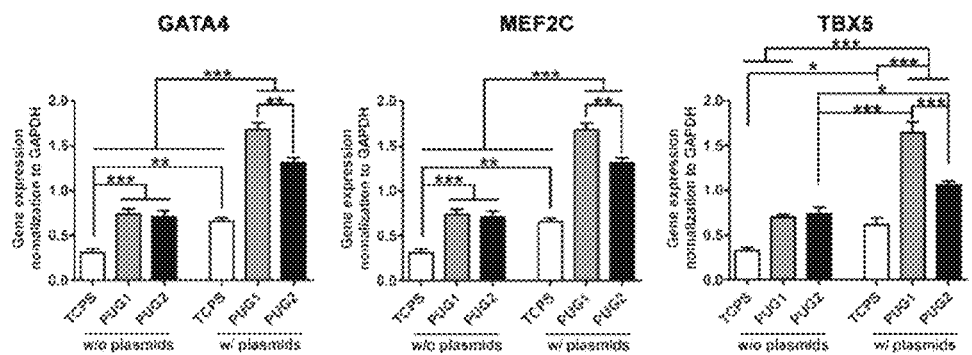
FIG. 30 shows the gene expression of cardiac-associated genes for hMSCs in PUG1, PUG2, and those on TCPS. The expression levels were normalized to the housekeeping gene (GAPDH). *, $p<0.05$; , $p<0.01$; *, $p<0.001$.

After hMSCs transfected in PU hydrogels or TCPS for 3 days, the gene expression of cardiac-associated genes was shown in FIG. 30. When the plasmids were absent, the 3 cardiac-associated gene expression levels in cells in PCL80DL20-1500 and PCL80DL20-2000 (~0.8) are higher than in TCPS (~0.3). While PCL80DL20-1500 or PCL80DL20-2000, cells and plasmids mixed well and through 27 G needle head to transfect, the 3 gene expression levels are higher than non-transfected cells. Among them, the gene expression level is highest in PCL80DL20-1500 (~1.8), then PCL80DL20-2000 (~1.3) and TCPS (0.8).

According to the embodiments above, this invention employed a waterborne process to successfully prepare PU NP dispersion based on PCL diol and PDLLA diol or one of the three different amphiphilic copolymer diols as the soft segment. All of them can form hydrogel at temperatures higher than 37° C., thus they can be used as 3D printing ink without adding any thickener. Further, they have good cytocompatibility as well as physico-chemical and mechanical properties, thus they are very suitable for a 3D cell and gene printing ink.

Example 9

The Synthesis of Biodegradable Polyurethane without Forming Block Copolymer

Figure 31:
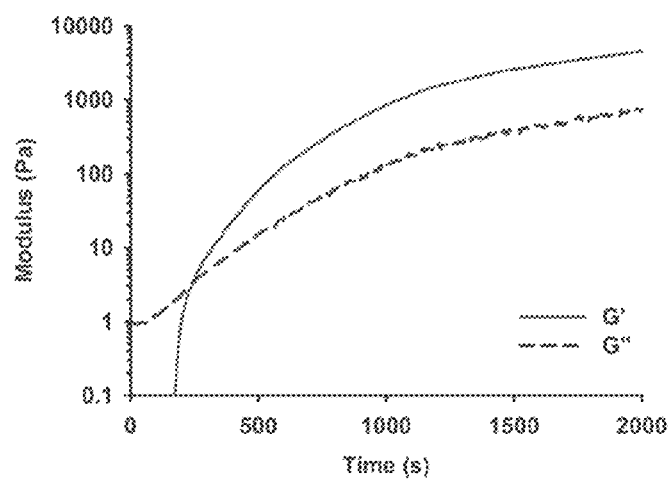
FIG. 31 shows time-dependent changes of storage modulus (G') and loss modulus (G") of PCL95EG5.

The present invention provides a synthesis of biodegradable polyurethane without forming block copolymer, as shown in Table 15 and FIG. 31, the biodegradable polyurethane is named PCL95EG5, the number behind the oligodiol abbreviation is the oligodiol's percentage of total soft segment. The storage modulus of PCL95EG5 at 37° C. for 20 min is 1553 Pa.

TABLE 15

Gelation time of PCL95EG5 (PCL diol:PEG diol = 95:5)

| Molecular weight (g/mol) | | Gelation time |
|---|---|---|
| PCL diol | PEG diol | (sec) |
| 2000 | 2000 | 242 |

Figure 32:
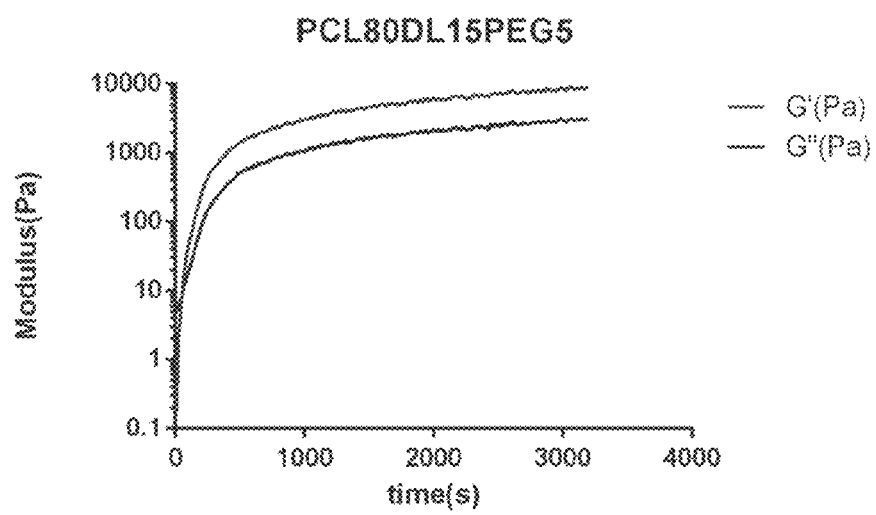
FIG. 32 shows time-dependent changes of storage modulus (G') and loss modulus (G") of PCL80DL15EG5.

The present invention provides another synthesis of biodegradable polyurethane without forming block copolymer, as shown in Table 16 and FIG. 32, the biodegradable polyurethane is named PCL80DL15EG5, the number behind the oligodiol abbreviation is the oligodiol's percentage of total soft segment. The storage modulus of PCL80DL15EG5 at 37° C. for 20 min is 3739 Pa.

TABLE 16

Gelation time of PCL80DL15EG5 (PCL diol:PDLLA diol:PEG diol = 80:15:5)

| Molecular weight (g/mol) | | | Gelation time |
|---|---|---|---|
| PCL diol | PDLLA diol | PEG diol | (sec) |
| 2000 | 1452 | 1450 | 58 |

Example 10

The Synthesis of Biodegradable Polyurethane with Polyhydroxybutyrate Diol

Figure 33:
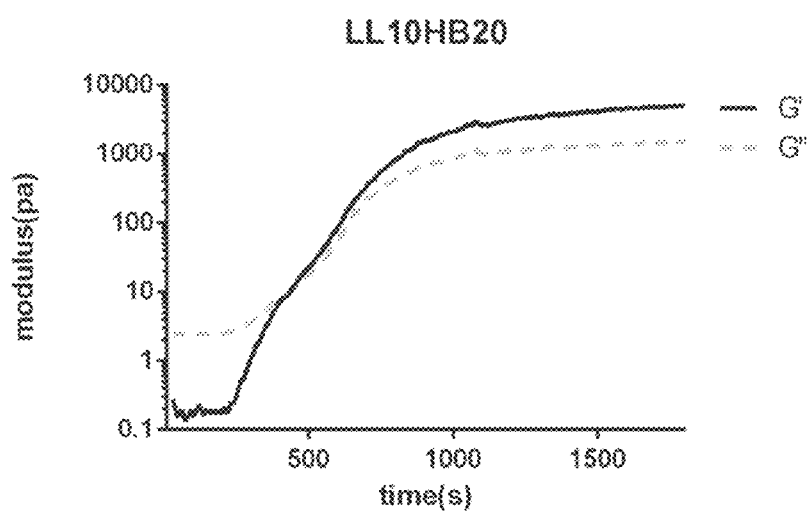
FIG. 33 shows time-dependent changes of storage modulus (G') and loss modulus (G") of PCL70LL10HB20.

The present invention further provides a synthesis of biodegradable polyurethane with polyhydroxybutyrate diol (PHB), as shown in Table 17 and FIG. 33, the biodegradable polyurethane is named PCL70LL10HB20, the number behind the oligodiol abbreviation is the oligodiol's percentage of total soft segment. The rheological property of PCL70LL10HB20 can maintain sol-gel transition phase for a longer period of time after sol-gel transition than other PU, and the time can be taken as a processing time, therefore, PCL70LL10HB20 results in a long processing time for applications. The storage modulus of PCL70LL10HB20 at 37° C. for 20 min is 2372 Pa.

TABLE 17

Gelation time of PCL70LL10HB20 (PCL diol:PLLA diol:PHB diol = 70:10:20)

| Molecular weight (g/mol) | | | Gelation time |
|---|---|---|---|
| PCL diol | PLLA diol | PHB diol | (sec) |
| 2000 | 2000 | 1438 | 441 |

What is claimed is:

1. A biocompatible and biodegradable elastomer, comprising: a main chain of polyurethane comprising a hard segment and a soft segment, the hard segment is formed by reaction of diisocyanate, 2,2-bis(hydroxymethyl)propionic acid and a chain extender, and the soft segment is a biodegradable oligomer diol, wherein the biodegradable oligomer diol is a combination consisting of 40~96 mol % polycaprolactone diol and 4~60 mol % polylactic acid diol, a combination consisting of 94~96 mol % polycaprolactone diol and 4~6 mol % poly(ethylene glycol) diol or a combination consisting of 78~84 mol % polycaprolactone diol, 12~18 mol % poly-DL-lactic acid diol and 4~6 mol % poly(ethylene glycol) diol;
wherein the polylactic acid diol has a molecular weight of 1040-2520 g/mol and poly(ethylene glycol) diol has a molecular weight of 1450-2400 g/mol; and
wherein the molar ratio of diisocyanate:soft segment:2,2-bis(hydroxymethyl)propionic acid:chain extender is 3-4:1:1-2:1.52.

2. The biocompatible and biodegradable elastomer of claim 1, wherein the polylactic acid diol is DL-lactic acid.

3. The biocompatible and biodegradable elastomer of claim 1, wherein the polylactic acid diol further synthesizing with poly(ethylene glycol) to form a block oligodiol, and the poly(ethylene glycol) has a molecular weight of 800-9600 g/mol.

4. The biocompatible and biodegradable elastomer of claim 3, wherein the polylactic acid diol is D-lactic acid or L-lactic acid.

5. The biocompatible and biodegradable elastomer of claim 3, wherein the block oligodiol is poly(L-lactide-co-polyethylene glycol) diol, poly(D-lactide-co-polyethylene glycol) diol, or poly(L-lactide-co-polyethylene glycol-co-L-lactide) diol.

6. The biocompatible and biodegradable elastomer of claim 3, wherein the block oligodiol is poly(L-lactide-co-polyethylene glycol) diol.

7. The biocompatible and biodegradable elastomer of claim 3, wherein the content of the block oligodiol is less than 24 mol % of soft segment.

8. The biocompatible and biodegradable elastomer of claim 3, wherein the content of the block oligodiol is 10 mol % of soft segment.

9. The biocompatible and biodegradable elastomer of claim 1, wherein the polylactic acid diol further synthesizing with polyhydroxybutyrate diol, and the polyhydroxybutyrate diol has a molecular weight of 1150-1725 g/mol.

10. The biocompatible and biodegradable elastomer of claim 1, wherein the diisocyanate is alicyclic polyisocyanate.

11. The biocompatible and biodegradable elastomer of claim 10, wherein the alicyclic polyisocyanate is isophorone diisocyanate.

12. The biocompatible and biodegradable elastomer of claim 1, wherein the chain extender is ethylenediamine.

13. A carrier made of the biocompatible and biodegradable elastomer of claim 1, wherein the carrier is present in the form of hydrogel, foam, electrospinning fiber, or scaffold.

14. The carrier of claim 13, wherein the carrier is used for carrying a cell or a gene.

* * * * *